United States Patent
Rooney et al.

(10) Patent No.: US 6,936,150 B2
(45) Date of Patent: Aug. 30, 2005

(54) METHODS AND APPARATUS FOR ELECTROPHORESIS OF PRIOR-CAST, HYDRATABLE SEPARATION MEDIA

(75) Inventors: Regina D. Rooney, La Jolla, CA (US); Bradley S. Scott, San Diego, CA (US); Joseph W. Amshey, Encinitas, CA (US); Thomas R. Jackson, La Jolla, CA (US); Sheldon Engelhorn, Cardiff, CA (US)

(73) Assignee: Invitrogen Corporation, Carlsbad, CA (US)

(*) Notice: Subject to any disclaimer, the term of this patent is extended or adjusted under 35 U.S.C. 154(b) by 0 days.

(21) Appl. No.: 10/102,188

(22) Filed: Mar. 18, 2002

(65) Prior Publication Data

US 2003/0015426 A1 Jan. 23, 2003

Related U.S. Application Data

(60) Provisional application No. 60/290,464, filed on May 10, 2001.

(51) Int. Cl.[7] ..................... G01N 27/447; G01N 27/453
(52) U.S. Cl. ..................... 204/466; 204/456; 204/606; 204/616; 204/618; 204/467
(58) Field of Search .......................... 204/467, 455, 204/456, 466, 470, 605, 606, 616, 617, 618, 459, 644

(56) References Cited

U.S. PATENT DOCUMENTS

| | | | |
|---|---|---|---|
| 3,875,044 A | 4/1975 | Renn et al. | 428/138 |
| 4,094,759 A | 6/1978 | Ruhenstroth-Bauer et al. | 436/516 |
| 4,130,470 A | 12/1978 | Rosengren et al. | 204/451 |
| 4,374,723 A | 2/1983 | Vesterberg | |
| 4,385,974 A | 5/1983 | Shevitz | |
| 4,417,967 A | 11/1983 | Ledley | 204/466 |
| 4,443,319 A | 4/1984 | Chait et al. | |
| 4,666,581 A | 5/1987 | Itoh et al. | |

(Continued)

FOREIGN PATENT DOCUMENTS

| | | | |
|---|---|---|---|
| DE | 19930253 A1 | 12/2000 | |
| WO | WO 98/57161 | 12/1998 | ......... G01N/27/447 |
| WO | WO 98/57162 | 12/1998 | ......... G01N/27/447 |
| WO | WO 99/33550 | 7/1999 | |
| WO | WO00/31526 | 6/2000 | ......... G01N/27/447 |
| WO | WO 01/20315 A1 * | 3/2001 | ................. 514/418 |
| WO | WO 02/26773 | 4/2002 | |

OTHER PUBLICATIONS

Amersham Pharmacia Biotech, "IPGphor IEF System," http://www.apbiotech.com/stiboasp/showmodule.asp? (Feb. 23, 2001).

Amersham Pharmacia Biotech, *2–D Electrophoresis Using Immobilized pH Gradients: Principles and Methods:* part 80–6429–60 (Sep. 1998).

BioRad, "PROTEAN® II xi and XL Multi–Cells: Ordering Information," http://www.bio-rad.com/B2B/BioRad/product/br category.jsp?BV. (Feb. 27, 2002).

(Continued)

*Primary Examiner*—Alex Noguerola
(74) *Attorney, Agent, or Firm*—Fish & Neave IP Group Ropes & Gray LLP; James F. Haley, Jr.; Tae Bum Shin

(57) ABSTRACT

Methods and apparatus are presented that facilitate electrophoresis of prior-cast, hydratable separation media, usefully immobilized pH gradient (IPG) strips. The method exploits the swelling of prior-cast, hydratable separation media upon rehydration to help lodge the media in an enclosing member that permits spaced electrical communication with the enclosed separation media. The electrical communication permits a voltage gradient to be established in the enclosed separation medium sufficient to effect separation of analytes therein. Cassettes, buffer cores, electrophoresis systems and kits are presented for effecting the methods of the invention.

36 Claims, 10 Drawing Sheets

U.S. PATENT DOCUMENTS

| | | | |
|---|---|---|---|
| 4,693,804 A | | 9/1987 | Serwer |
| 4,746,551 A | * | 5/1988 | Allen et al. .................. 204/456 |
| 5,149,418 A | * | 9/1992 | Flesher ........................ 204/618 |
| 5,159,049 A | | 10/1992 | Allen |
| 5,209,831 A | | 5/1993 | MacConnell ................ 204/616 |
| 5,238,651 A | | 8/1993 | Chuba .......................... 422/61 |
| 5,275,710 A | | 1/1994 | Gombocz et al. |
| 5,407,546 A | | 4/1995 | Schickle |
| 5,543,023 A | | 8/1996 | Lugojan ...................... 204/618 |
| 5,593,838 A | | 1/1997 | Zanzucchi et al. ............. 435/6 |
| 5,699,157 A | | 12/1997 | Parce .......................... 356/344 |
| 5,746,901 A | | 5/1998 | Balch et al. ................. 204/606 |
| 5,773,645 A | | 6/1998 | Hochstrasser |
| 5,800,690 A | | 9/1998 | Chow .......................... 204/451 |
| 5,827,418 A | * | 10/1998 | Haven et al. ................ 204/618 |
| 5,837,116 A | | 11/1998 | Harrington et al. ......... 204/606 |
| 5,888,369 A | | 3/1999 | Tippins et al. .............. 204/606 |
| 5,989,400 A | | 11/1999 | Islam .......................... 204/466 |
| 6,001,233 A | | 12/1999 | Levy .......................... 204/618 |
| 6,013,165 A | | 1/2000 | Wiktorowicz et al. ...... 204/456 |
| 6,113,766 A | | 9/2000 | Steiner et al. ............... 204/606 |
| 6,156,182 A | | 12/2000 | Olech et al. ................ 204/610 |
| 6,398,933 B1 | | 6/2002 | Scott |
| 6,558,522 B1 | | 5/2003 | Williams et al. |

OTHER PUBLICATIONS

BioRad, *PROTEAN®II xi Cell and PROTEAN II xi 2–D Cell Instruction Manual.*

BioRad, "2–D Electrophoresis: ReadyStrip™ IPG Strips: Part of the ProteomeWorks™ System."

BioRad, "Protean II xi multi–cell Instruction Manual: CXatalog No. 165–1951."

BioRad, "A Flexible, High Throughput Method For 2–D Protein Separations," *EG Bulletin 2217.*

BioRad, "PROTEAN II XL Cell for IPG Strips," http://www.bio–rad.com/B2B/BioRad/product/br category.jsp?BV (Feb. 23, 2002).

BioRad, "PROTEAN® IIxi Cell IPG Conversion Kit Setup Guide."

BioRad, "The ProteomeWorks™ Systems: Now Get More from 2–D."

BioRad, "Protein Electrophoresis: Large Precast Gels for 2–D: Part of the Proteome Works™ System, Ready Gel Precast Gels for Two–Dimensional Gel Electrophoresis."

BioRad, "Protein Electrophoresis: Large Precast Gels for 1–D, Protean® II Ready Gel™ Precast Gels for Single–Dimension Gel Electrophoresis."

BioRad, "2–D Electrophoresis: Ready Strip™ IPG Strips: Part of the Proteome™ System."

BioRad, "ReadyStrip™ IPG Strips Instruction Manual: Catalog No. 163–2099."

Bjellqvist et al., "Isoelectric Focusing in Immobilies pH Gradients: Principle, Methodology and Some Applications," *Journal of Biochemical and Biophysical Methods* 6(4): 317–339 (1982).

Bonnet et al., "Epoxy–Diamine Thermoset/Thermoplastic Blends: Dielectric Properties before, during, and after Phase Separation." *Maromolecules* 33(10): 3833–3843 (2000).

Bonnet et al., "Epoxy–Diamine Thermoset/ thermoplastic Blends. 2. Rheological Behavior befroe and after Phase Separation." *Macromolecules* 32(25): 8524–8530 (1999).

Bonnet et al., "Epoxy–Diamine Thermoset/Thermoplastic Blends. 1. Rates of Reaction before and after Phase Separation," *Macromolecules* 32(25): 8517–8523 (1999).

Gorg et al., "The Current State of Two–Dimensional Electrophoresis with Immobilized pH Gradients," *Electrophoresis* 21(6): 1037–1053 (Apr. 2000).

Gorg et al., "The Current State of Two–Dimensional Electrophoresis with immobilied pH Gradients," *Electrophoresis*9(9): 531–546 (1988). month unknown.

Haglund, Herman, "Isoelectric Focusing In pH Gradients–A Technique for Fractionalization and Characterization of Ampholytes," Methods of Biochemical Analysis vol. 19, Interscience Publishers.

Holter et al., "Liquid Crystalline Thermosets Based on Branched Bismethacrylates," *Macromolecules* 29(22): 7003–7011 (1996). month unknown.

Invitrogen Life Technologies, "Xcell SureLock™ Mini–Cell: The Most Convenient, Versatile, Mini–Vertical Electrophoresis System," *http://www.invitrogen.com/content.cfm?pageid=3476&cfid=1359647&cftoken=23915763* (Apr. 18, 2001).

Islam et al., "A New Approach to Rapid Immobiled pH Gradient IEF for 2–D Electrophoresis," *Science Tools from Amersham Pharmacia Biotech* 3(1): 14–15 (1998). month unknown.

Righetti et al, "Isoelectric Focusing in Gels," *Journal of Chromatography* 98(2): 271–321 (Sep. 25, 1974).

Righetti et al., "Isoelectric Focusing in Immobilized ph Gradients: An Update," *Journal of Chromatography B* 669(1–2): 77–89 (Oct. 10, 1997). month unknown.

Righetti et al., "Isoelectic Focusing in ImmobilizedpH Gradients," *Methods in Enzymology* 270: 235–255 (1996). month unknown.

Righetti et al., "Immobilized pH Gradients," *Trends in Biochemical Science* 13(9): 335–338 (1988). Sep.

Yoon et al., "Effect to Thermal History of the Rheological Behavior of Thermoplastic Polyurethanes," *Macromolecules* 33(6): 2171–2183 (2000). month unknown.

Frey et al., "Preparation of Rehydratable Polyacrylamide Gels and Their Application in Ultrathin–layer Isoelectric Focusing", Electrophoresis 7:28–40 (1986).

U.S. Appl. No. 09/633,172, filed Aug. 2000, Champagne.

* cited by examiner

METHODS AND APPARATUS FOR ELECTROPHORESIS OF PRIOR-CAST, HYDRATABLE SEPARATION MEDIA

CROSS REFERENCE TO RELATED APPLICATIONS

This application claims the benefit of U.S. provisional application Ser. No. 60/290,464, filed May 10, 2001.

FIELD OF THE INVENTION

The present invention relates to methods and apparatus for electrophoresis of prior-cast hydratable separation media. In particular, the invention relates to methods, cassettes, buffer cores, and systems useful for conducting isoelectric focusing using immobilized pH gradient (IPG) strips.

BACKGROUND OF THE INVENTION

For over thirty years, isoelectric focusing (IEF) has served as a primary tool for analyzing proteins present in complex admixture, such as proteins present in biological samples.

In isoelectric focusing, proteins are driven by an applied electric field through a pH gradient typically established in a support matrix, such as a gel. Proteins migrate until the isoelectric point (pI) of the protein coincides with the local pH; at that point, the protein no longer bears net charge and ceases to migrate, becoming focused at a point that is characteristic of the protein.

As originally described, the pH gradient for IEF was established and sustained in the gel matrix by mobile carrier ampholytes (CA). Gels typically would be polymerized in the presence of a population of CA having a range of charge characteristics; upon application of a voltage gradient, the various species of CA would align themselves in the matrix to establish a pH gradient across the gel.

Although IEF with CA has proven tremendously useful, it was soon discovered that pH gradients created by CA were susceptible to titration by atmospheric carbon dioxide, leading to the migration of CA towards the cathode and destruction of the pH gradient over time, a phenomenon termed cathodic drift.

Cathodic drift can be reduced by casting IEF gels in enclosed tubes, thus limiting exposure to atmospheric $CO_2$. However, the tube traps prepolymer component impurities in the matrix during polymerization, interfering with separation. Furthermore, the tube format presents difficulties when a second dimension of separation, such as fractionation by size, is desired.

In a different approach to the problem of cathodic drift, Bjellqvist and colleagues immobilized the pH gradient in the support matrix, an approach now termed immobilized pH gradient (IPG) isoelectric focusing. See Bjellqvist et al., *J. Biochem. Biophys. Methods* 6(4):317–39 (1982); Righetti et al., *Trends Biochem. Sci.* 13(9):335–8 (1988); Righetti et al., *Methods Enzymol.* 270:235–55 (1996); U.S. Pat. No. 4,130,470; and Righetti, *Immobilized pH Gradient: Theory and Methodology*, (Laboratory Techniques in Biochemistry and Molecular Biology, Vol. 20), Elsevier Biomedical Press, LTD, Netherlands (ASIN: 0444813012). Two-dimensional electrophoresis, with IPG IEF followed by size fractionation, soon followed. Gorg et al., *Electrophoresis* 9(9):531–46 (1988).

IPG not only reduced the problem of cathodic drift, but also proved useful in reducing interference from prepolymer component impurities, since the IPG strip's plastic backing imparts sufficient structural resilience to the gel as to permit the gel to be washed before use. The increased resilience also permits the gels to be stored in dehydrated form before use. Dehydrated IPG strips are today sold in a variety of pH ranges and a variety of separation lengths by a number of vendors (e.g., Immobiline DryStrip Gels, Amersham Pharmacia Biotech, Piscataway, N.J., USA; ReadyStrip IPG, Bio-Rad Laboratories, Hercules, Calif., USA). Problems remain, however.

Although immobilization of the gradient-forming ampholytes prevents cathodic drift, the charge-bearing immobilized moieties (immobilines) remain susceptible to titration by atmospheric $CO_2$. $CO_2$ titration is exacerbated by the fact that the separation medium of IPG strips is directly exposed to air on at least one side. Direct exposure to air also leads to possible dehydration of the matrix, with possible salt crystallization, during electrophoresis.

These problems have been addressed in part by a methodologic, rather than structural, solution: plastic-backed IPG strips are typically electrophoresed under an occlusive oil layer, which both excludes air and retards evaporation.

Use of an occlusive liquid oil layer presents its own difficulties, however. Principal among these is the requirement that electrophoresis be performed with the IPG strip maintained in a horizontal orientation. The obligate horizontal orientation precludes use of the smaller-footprint, vertical electrophoresis devices typically used for SDS-polyacrylamide gel electrophoresis (SDS-PAGE), such as those described in Tippins et al., U.S. Pat. No. 5,888,369. In addition, the use of oil requires deft manual technique and proves time-intensive.

Wiktorowicz et al., U.S. Pat. No. 6,013,165, describe an apparatus in which immobilized pH gradient isoelectric focusing can be performed without use of a liquid oil layer. A continuous pKa gradient is immobilized on at least one of the major opposing surfaces of a cavity formed between two plates. The cavity, which can be further segmented into parallel channels, is then filled with a flowable separation medium. Electrophoresis is preferably conducted with the assembly oriented horizontally to minimize convection currents in the flowable separation medium. The apparatus does not readily permit insertion of prior-cast hydratable separation media, such as commercial IPG strips, nor does it readily permit electrophoresis in the vertical dimension.

There thus exists a need in the art for methods and apparatus that allow IPG strips, and other prior-cast hydratable separation media, to be electrophoresed without requiring contact with an occlusive fluid oil layer. There further exists a need in the art for methods and apparatus that allow IPG strips, and other prior-cast hydratable separation media, to be electrophoresed in a vertical orientation.

SUMMARY OF THE INVENTION

The present invention solves these and other needs in the art by providing methods, apparatus, and kits for electrophoresis of prior-cast hydratable separation media that obviate the use of an occlusive oil layer, thereby obviating the requirement that electrophoresis be performed in the horizontal orientation.

The present invention is based, in part, upon the discovery that the swelling that attends rehydration of prior-cast hydratable separation media can be exploited to help lodge such media in an enclosure that permits spaced electrical communication with the enclosed separation medium. The spaced electrical communication makes it possible to apply a voltage gradient to the prior-cast hydratable separation media while the medium is otherwise enclosed, permitting electrophoresis to be conducted within a cassette.

Enclosed, the separation medium's contact with air is substantially reduced. In cases in which the prior-cast hydratable separation medium is an IPG strip, the reduction in air contact obviates the prior art requirement for occlusive contact with a fluid oil layer during immobilized pH gradient isoelectric focusing.

Enclosed, and lacking an attendant fluid oil layer, the prior-cast separation medium can be electrophoresed in any physical orientation. In cases in which the prior-cast hydratable separation medium is an IPG strip, relaxation of the prior-art requirement for horizontal electrophoresis makes it newly possible to perform IPG electrophoresis using the widely distributed, small footprint, vertical electrophoresis gel boxes presently used to perform SDS-PAGE.

Thus, in a first aspect, the invention provides a method for performing electrophoresis, comprising: hydratingly lodging a prior-cast hydratable electrophoretic separation medium within an enclosing member that permits spaced electrical communication with the enclosed medium; and then using the spaced electrical communication to establish a voltage gradient in the enclosed separation medium sufficient to effect electrophoretic separation of analytes therein.

In one embodiment, the method further comprises the antecedent step of inserting the prior-cast hydratable electrophoretic separation medium in its dehydrated state into the enclosing member. In another embodiment, the method further includes a later step of removing the prior-cast hydratable electrophoretic separation medium from the enclosing member. The medium once removed can be used, for example, to apply the one-dimensionally fractionated sample to a gel to effect a second dimension of separation.

In some embodiments, the step of hydratingly lodging comprises: contacting the dehydrated prior-cast hydratable electrophoretic separation medium with an aqueous solution, often an aqueous solution that includes the sample to be fractionated.

The methods of the present invention are particularly useful in performing isoelectric focusing using immobilized pH gradient strips. Thus, the prior-cast hydratable electrophoretic separation medium used in the practice of the present invention can usefully have an immobilized pH gradient.

As described above, the methods of the present invention include the use of an enclosing member that has (i) means for hydratingly lodging a prior-cast electrophoretic separation medium therewithin, and (ii) means for spaced electrical communication with the enclosed separation medium, wherein the spaced electrical communication means can be used to apply a voltage gradient to the enclosed medium sufficient to effect electrophoretic separation of analytes present therewithin.

Thus, in another aspect, the invention provides a cassette for performing electrophoresis, comprising: means for hydratingly lodging a prior-cast electrophoretic separation medium within an enclosing member; and means for spaced electrical communication with the enclosed medium, wherein the spaced electrical communication means can be used to establish a voltage gradient in the separation medium sufficient to effect electrophoretic separation of analytes therein.

In certain embodiments, the cassette of the present invention comprises: a form-retaining member, and at least one channel, wherein the form-retaining member imparts dimensional integrity to the channel or channel(s). In typical embodiments, the cassette includes a plurality of such channels.

Each channel present in the cassette and useful for performing the methods of the present invention has a first channel entry, a second channel entry, and a cavity therebetween, the channel cavity being so dimensioned as to permit insertion of a hydratable prior-cast electrophoretic separation medium in its dehydrated state and lodgingly enclose the strip in its rehydrated state. The first and second channel entries permit spaced electrical communication with the channel cavity; the spaced electrical communication permits current to be flowed through the channel cavity.

In some embodiments, the form-retaining member contributes the entire circumferential wall of the cavities of the channels. In other, multilaminate embodiments, the cassette further comprises a laminate cover; the laminate cover adheres directly or indirectly to the form-retaining member and contributes at least part of the circumferential wall of said channels. In these latter embodiments, the adherence of the laminate cover to the form-retaining member is typically reversible.

In other embodiments, the cassette further comprises a first well-forming member, which adheres directly or indirectly to the form-retaining member, and which defines fluid reservoirs at a plurality of first channel entries. Usefully, the cassette can further comprise a second well-forming member, the second well-forming member adhering, directly or indirectly, to the form-retaining member and defining fluid reservoirs at a plurality of second channel entries. When present, the well-forming members can usefully be reversibly adherent to the form-retaining member.

In one series of related embodiments, the first and second channel entries for each of the channels permit electrical communication with the intervening channel cavity through a common surface of the cassette. In another series of related embodiments, the first and second channel entries permit electrical communication with their intervening cavity through separate surfaces of the cassette. These two mutually exclusive geometries call for different electrode geometries, and thus different electrophoresis buffer cores, to complete the circuits required for electrophoresis.

The prior-cast hydratable electrophoretic separation medium can be provided by the user, can be included within one or more channels of the cassette without requirement for user insertion thereof, or can be provided separately packaged with the cassette in a kit.

As to the latter, it is another aspect of the present invention to provide kits for facilitating electrophoresis of prior-cast hydratable electrophoretic separation media. The kits typically comprise a cassette of the present invention and at least one prior-cast hydratable electrophoretic separation medium suitably dimensioned as to be hydratingly lodgeable in said cassette.

In some embodiments, the kit includes a cassette and at least one conductive wick for use therewith; often, in such kits, a sufficient number of wicks are provided to facilitate both anodic and cathodic connections with the cassette.

The cassettes of the present invention can be used to effect vertical electrophoresis of prior-cast hydratable separation media, usefully in the buffer tanks that are commonly used, with buffer cores, for SDS-PAGE electrophoresis. In cassette embodiments in which the first and second channel entries open to separate surfaces of the cassette, buffer cores presently used for SDS-PAGE electrophoresis can be used.

In cassette embodiments in which the first and second channel entries open to the same surface of the cassette, alternative buffer core geometries are required.

Thus, it is another aspect of the present invention to provide a buffer core for vertical electrophoresis of pre-cast hydratable electrophoretic separation media, comprising: a substantially inflexible frame, an anode, and a cathode in spaced relationship to the anode. The buffer core frame has a first cassette engagement face and a second cassette engagement face. Operational engagement of a first and second cassette to the respective first and second frame engagement faces creates a chamber internal to the frame that is sealed on 5 sides. The cathode and anode are each in electrical communication with the interior of the internal chamber, and operational engagement of a first and second cassette to the respective first and second frame engagement faces causes spaced contact of the anode and cathode to the surface of at least one cassette that engages the frame engagement surface, allowing electrophoresis of prior-cast hydratable separation media enclosed therein.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

DETAILED DESCRIPTION

Figure 1:
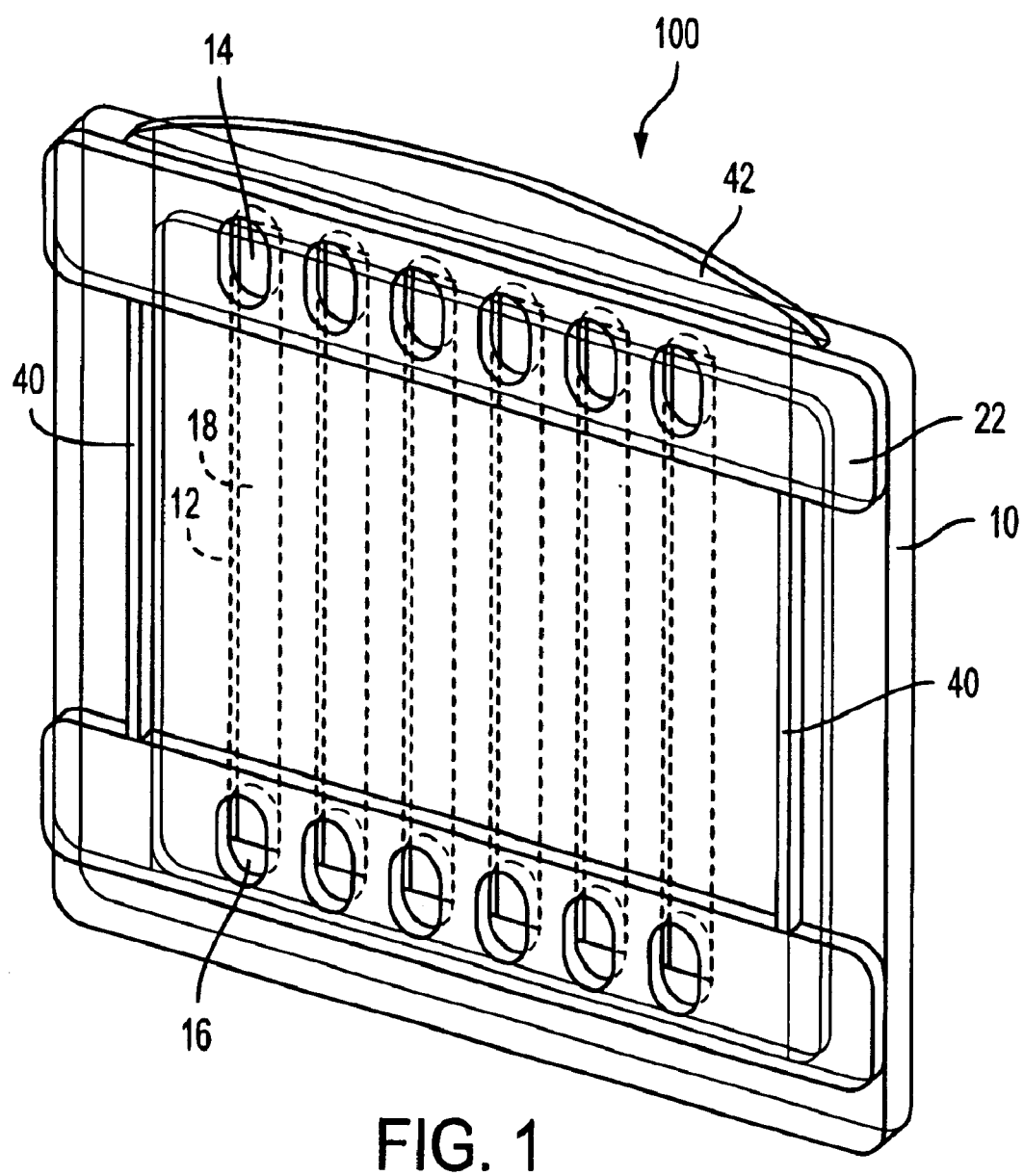
FIG. 1 is a front perspective view of a cassette of the present invention.

The present invention is based, in part, upon the discovery that the swelling that attends rehydration of prior-cast hydratable separation media can be exploited to help lodge such media in an enclosure that permits spaced electrical communication with the enclosed separation medium. The spaced electrical communication makes it possible to apply a voltage gradient to the prior-cast hydratable separation media while the medium is lodged within the enclosing member.

Enclosed, the separation medium's contact with air is substantially reduced. In cases in which the prior-cast hydratable separation medium is an IPG strip, the reduction in air contact obviates the prior art requirement for occlusive contact with a fluid oil layer during immobilized pH gradient isoelectric focusing.

Enclosed, and lacking an attendant fluid oil layer, the prior-cast separation medium can be electrophoresed in any physical orientation. In cases in which the prior-cast hydratable separation medium is an IPG strip, relaxation of the prior-art requirement for horizontal electrophoresis makes it newly possible to perform IPG electrophoresis using the widely distributed, small footprint, vertical electrophorosis gel boxes presently used to perform SDS-PAGE.

In a first aspect, therefore, the invention provides a method for performing electrophoresis, particularly for performing electrophoresis using prior-cast, hydratable separation media. As used herein, the term "electrophoresis" explicitly includes isoelectric focusing.

In a first step, the method comprises hydratingly lodging a prior-cast hydratable electrophoretic separation medium within an enclosing member that permits spaced electrical communication with the enclosed media. In a second step, the spaced electrical communication is used to apply a voltage gradient to the enclosed medium sufficient to effect electrophoretic separation of analytes therein.

As used herein, the phrase "prior-cast electrophoretic separation medium" (and equivalently, "prior-cast separation medium") refers to an electrophoretic separation medium, typically a polymeric gel, that has first been solidified, or gelled, elsewhere than in the enclosing member in which electrophoresis is to be performed.

Electrophoretic separation media, and methods of preparing, casting, and performing electrophoresis using electrophoretic media, are well known in the analytical arts, and need not be detailed here. See, e.g., Rabilloud (ed.), *Proteome Research: Two-Dimensional Gel Electrophoresis and Identification Methods*, Springer Verlag, 2000 (ISBN: 3540657924); Westermeier, *Electrophoresis in Practice*, 2nd ed., John Wiley & Sons, 2000 (ISBN 3527300708); B. D. Hames et al. (eds.), *Gel Electrophoresis of Proteins*, 3rd ed., Oxford University Press, 1998) (ISBN 0199636419); and Jones, *Gel Electrophoresis: Nucleic Acids: Essential Techniques*, (John Wiley & Son Ltd. 1996) (ISBN 0471960438), the disclosures of which are incorporated herein by reference in their entireties.

Although polyacrylamide (that is, a polymerization product of acrylamide monomer crosslinked with N,N'-methylenebisacrylamide) and agarose are the two polymeric gels most commonly used in electrophoresis today, the present invention proves useful in electrophoresing a far wider variety of polymeric gels.

Because the gel is first solidified, or gelled, elsewhere than in the enclosing member in which electrophoresis is to be performed, the "prior-cast electrophoretic separation medium" used in the present invention must have sufficient structural resiliency to be transferred or released from its casting mold and thereafter lodged within the enclosure of the present invention.

Typically, such structural resiliency will be imparted to the separation medium by the adherence thereto or incorporation therein of a layer or lamina of another material, such as plastic. Such layers are known in the art, and include, e.g., polyester film backings, as are found in commercial IPG strips, and polyester mesh fabric, which can be incorporated into the separation medium.

Although the "prior-cast electrophoretic separation medium" used in the present invention is typically fashioned as a strip—that is, with a first dimension substantially greater than a second dimension—such dimensions are not required for practice of the present invention. Nonetheless, for ease of description, all prior-cast electrophoretic separation media useful in the practice of the present invention are referred to in the alternative herein as "strips".

A "prior-cast hydratable electrophoretic separation medium" is a prior-cast electrophoretic medium that can be dehydrated and that, after rehydration, has retained sufficient structural integrity to permit electrophoretic separation of analytes there within.

Neither complete removal of moisture, during dehydration, nor complete saturation with liquid, during rehydration, is required or intended. It suffices for practice of the present invention that the prior-cast, hydratable, electrophoretic separation medium swell detectably after contact in its dehydrated state with an aqueous solution ("aqueous buffer", "buffer").

Typically, the prior-cast hydratable electrophoretic separation medium will swell at least about 5% in volume, often at least about 10%, 15%, 20%, even at least about 25%, 30%, 40% or more in volume upon contact with an aqueous buffer. The volume increase can be manifest in all three dimensions or, when the separation medium is backed with an inextensible layer, principally in one or in two dimensions. The volume increase can occur over a period of minutes or, in the case of IPG strips, more typically over a period of hours.

The degree of swelling is sufficient if the prior-cast, hydratable, electrophoretic separation medium swells sufficiently upon contact with an aqueous solution ("aqueous buffer", "buffer") as to permit hydratable lodging in an enclosing member.

By "hydratable lodging" is intended that the prior-cast, hydratable separation medium be insertable into an enclosing member in its dehydrated state, and that it become lodged in the enclosing member in its rehydrated state.

Although the strip must be "insertable" in its dehydrated state, the strip need not necessarily be removable from the enclosing member in its dehydrated state.

The rehydrated prior-cast hydratable separation medium is said to be "lodged" in the enclosing member (equivalently, "lodgingly enclosed" therein) when two conditions are met. First, the strip remains within the enclosing member when the enclosing member is brought into vertical orientation. Second, when the enclosing member is brought into vertical orientation, at least 50% of the separation medium is precluded from direct communication with ambient atmosphere. Furthermore, although frictional and surface tension forces between the rehydrated separation medium and the enclosing member can contribute to the strip's lodging therein, it is not intended that such frictional or surface tension forces be sufficient in themselves to effect lodging of the strip within the enclosing member.

The enclosing member will be sufficiently form-retaining as to be able to maintain dimensional integrity when maintained in contact with a prior-cast, hydratable separation medium that is swelling. In certain embodiments described in detail below, the enclosing member is a cassette having a form-retaining channel cavity within which the prior-cast, hydratable separation medium is engaged.

The enclosing member further permits spaced electrical communication with the enclosed prior-cast hydratable separation medium. Communication can be direct, as by through-passage of anode and cathode electrodes, or indirect, as by passage of current through an intermediate polymer layer or wick, as will be further discussed below.

After the prior-cast hydratable electrophoretic separation medium is lodged in the enclosing member, the spaced electrical communication is used to apply a voltage gradient sufficient to effect electrophoretic separation of analytes therein.

Although described particularly herein as application of a voltage gradient to the separation medium, it is understood that current is thereby caused to flow through the separation medium, and that the method could equally be described as flowing current through the separation medium.

The electrical parameters to be used depend upon the composition and dimensions of the enclosed electrophoretic medium, the composition of the sample, the composition of the rehydration solution, and the type of desired separation, and is thus determined using factors well known in the electrophoretic arts.

For example, in cases in which the prior-cast hydratable electrophoretic medium is a 70 mm Immobiline DryStrip gel having pH range of 4–7 (Amersham Pharmacia Biotech, Piscataway, N.J., USA), a typical protocol would be to apply 200 V for 1 minute, ramping up to 3500 V over 1½ hours, followed by 3500 V for 55 minutes to 1½ hours, all with current limited to 2 mA. Other protocols can be found, e.g., in *2-D Electrophoresis Using Immobilized pH Gradients: Principles and Methods*, Amersham Pharmacia Biotech (part 80-6429-60; Rev. A, September 1998), the disclosure of which is incorporated herein by reference in its entirety.

Returning to the method in more detail, the prior-cast hydratable electrophoretic separation medium is typically inserted by the user in its dehydrated state in the enclosing member.

By way of example, in embodiments further described below, the prior-cast hydratable separation medium, such as an IPG strip, is movably inserted by hand into a channel cavity present within the enclosing member. As another example, where the enclosing member is hinged, or otherwise reversibly separable, the prior-cast hydratable separation medium, such as an IPG strip, is movably inserted by hand into a depression, with the channel cavity thereafter completed by closing the member.

Although typical, movable insertion of the dehydrated strip into the enclosing member is not always required. For example, the dehydrated strip can be earlier-inserted during manufacture of the enclosing member, obviating insertion of the dehydrated prior-cast separation medium into the enclosing member by the user.

The dehydrated separation medium is then contacted with an aqueous solution.

The composition of the rehydration solution will depend upon the composition of the sample and separation medium and the intended electrophoretic procedure, and its choice will thus depend on factors that are well known in the electrophoretic arts.

For example, where the prior-cast hydratable separation medium is a commercial IPG strip, such as an Immobiline DryStrip (Amersham Pharmacia Biotech, Piscataway, N.J., USA), the rehydration solution can usefully include urea, non-ionic or zwitterionic detergents, dithiothreitol (DTT), dye, and a carrier ampholyte mixture suited to the pH range of the IPG strip. Carrier ampholyte mixtures for use in such rehydration solutions are available commercially (e.g., IPG Buffer pH 3.5–5.0, cat. no. 17-6002-02; IPG Buffer pH 4.5–5.5, cat. no. 17-6002-04; IPG Buffer pH 5.0–6.0, cat. no. 17-6002-05; IPG Buffer pH 5.5–6.7, cat. no. 17-6002-06; IPG Buffer pH 4–7, cat. no. 17-6002-86; IPG Buffer pH 6–11, cat. no. 17-6002-78; IPG Buffer pH 3–10 NL, cat. no. 17-6002-88; IPG Buffer pH 3–10, cat. no. 17-6002-87, all from Amersham Pharmacia Biotech, Piscataway, N.J., USA).

The rehydration solution can also advantageously include the sample intended to be separated in the prior-cast hydratable separation medium.

For example, in cases in which the prior-cast hydratable electrophoretic separation medium is an IPG strip, the sample to be separated can be a mixture of proteins, such as those from a biological sample, and can usefully be or have been denatured, as by chaotropes, reducing agents, and detergents. In cases in which the separation medium is other than an immobilized pH gradient strip, the sample can include other types of macromolecules, such as nucleic acids.

The methods of the present invention can include the later step of removing the prior-cast hydratable separation medium from the enclosing member after electrophoresis. The method of removal will depend on the structure of the enclosing member, as will be further described below. As an alternative to removal, the separation medium in certain embodiments of the methods of the present invention can be further analyzed within the enclosing member, such as by staining and drying.

As described above, the methods of the present invention include the use of an enclosing member that has (i) means for hydratingly lodging a prior-cast electrophoretic separation medium therewithin and (ii) means for spaced electrical communication with the enclosed separation medium, wherein the spaced electrical communication means can be used to apply a voltage gradient to the enclosed separation medium sufficient to effect electrophoretic separation of analytes present therewithin.

It is, therefore, another aspect of the present invention to provide an enclosing member useful in the practice of the methods of the present invention, which enclosing member is hereinafter called a "cassette".

FIG. 1 is a front perspective view of an embodiment of a cassette of the present invention.

Cassette 100 comprises form-retaining member 10 and at least one channel 12 (in the embodiment shown in FIG. 1, cassette 100 has six substantially parallel channels 12, although fewer or greater numbers can be present). Form-retaining member 10 imparts dimensional integrity to prior-formed channels 12.

Referring again to FIG. 1, channel 12 has first channel entry 14 and second channel entry 16 and cavity 18 therebetween. Cavity 18 of channel 12 is so dimensioned as to movingly engage a prior-cast hydratable electrophoresis medium ("strip"), such as an IPG strip, in its dehydrated state, and to lodgingly enclose the strip after hydration thereof.

First channel entry 14 and second channel entry 16 permit electrical communication with cavity 18, and thus define a channel current flow axis through cavity 18. In certain embodiments of cassette 100 particularly designed for use with buffer cores of the prior art (see below), the channel current flow axis is in a plane substantially parallel to a substantially planar first surface of form-retaining member 10.

To use cassette 100 in the methods of the present invention, rehydratable electrophoresis strip 20, such as an IPG strip, is inserted in its dehydrated state into channel 12, typically through entry 14 or entry 16. In alternative embodiments, strip 20 has been prior-inserted into cassette 100, either by the user or by the manufacturer thereof.

Strip 20 is rehydrated within channel 12 by application of a rehydration solution, optionally containing the sample to be fractionated.

Rehydration solution is typically dispensed into channel 12 prior to insertion of strip 20, since insertion of strip 20 into channel 12 is facilitated by wetting of the interior of channel 12. Strip 20 can, however, be prior-inserted into channel 12, with rehydration solution thereafter applied at either or both of entries 14 and 16. For samples requiring long rehydration times, entry 14, entry 16, or both can be sealed—e.g. with tape or cover slip—to prevent evaporation and the accidental discharge of rehydration solution.

Upon rehydration, strip 20 becomes lodged in cavity 18 of channel 12, at least in part due to swelling of the separation medium. Strip 20 is thereafter not readily removed from channel 12 without expansion of cavity 18, as further described below.

If the sample to be electrophoretically fractionated is not included in the rehydration solution, sample is then applied at entry 14, entry 16, or both with the cassette oriented horizontally to retain sample, and allowed to enter the separation medium. Alternatively, sample can be prior-absorbed into a wick which is then inserted into entry 14, entry 16, or both, from which wick the sample then enters the separation medium. As further described below, sample entry can be facilitated by application of electrical current.

Electrophoresis is then performed by applying a voltage gradient to strip 20, causing current to flow along the channel current flow axis.

Thereafter, strip 20 is typically removed from channel 12 for further processing, such as staining and/or contacting of strip 20 (or a portion thereof) to a gel to effect separation along a second dimension. Removal is typically effected by expansion of cavity 18 using a method appropriate to the composition of cassette 100; for example, in embodiments of cassette 100 in which one or more laminae contribute to the circumferential walls of cavity 18, removal can be effected by peeling of the laminae, thus opening channel 12. For certain purposes, further processing can be effected within channel 12.

Returning to FIG. 1, form-retaining member 10 is constructed of form-retaining nonliquid materials. Preferred materials are those that are readily machined, molded, or etched, that are chemically compatible—that is, do not suffer substantial degradation upon contact—with electrophoretic buffer systems, that do not appreciably bind or impede the transport of analytes through the enclosed gel, and that provide a vapor gas barrier. Usefully, form-retaining member 10 can be constructed from translucent, or transparent material, including optical quality transparent material, thus permitting strip 20 to be visualized while engaged in cavity 18. Typically, form-retaining member 10 is constructed of materials that are substantially electrically nonconducting, thus reducing or eliminating the concurrent action on strip 20 of electrical fields other than those along the channel current flow axis through cavity 18.

In typical embodiments, form-retaining member 10 is composed of ceramic, quartz, glass, silicon and its derivatives, plastic, or mixtures thereof. Among plastics useful in the construction of form-retaining member 10 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, polyester, and mixtures or copolymers thereof.

Form-retaining member 10 is also usefully composed of materials that permit heat to be conducted away from strip 20 during electrophoresis. In that regard, form-retaining member 10 can usefully be shaped to include recessed region 27, shown in FIG. 3A and particularly in FIG. 3B, reducing the thickness of form-retaining member 10 in regions proximal to channels 12, reducing thermal resistance between strip 20 and a heat sink, usefully a fluid filled chamber, as further discussed below.

Form-retaining member 10 confers dimensional integrity upon channels 12. Dimensional integrity is important to permit the dispensing into channel 12 of rehydration solution (optionally with sample to be fractionated), to permit strip 20 to be inserted into channel 20, and to effect hydratable lodging of strip 20 in channel 12 upon rehydration.

Form-retaining member 10 can confer dimensional integrity upon channel 12 by contributing at least a portion of the circumferential wall of cavity 18 of channel 12.

For example, cavity 18 of channel 12 can be constructed as a tunnel, bore, or conduit within form-retaining member 10. In such embodiments, form-retaining member 10 contributes the entirety of the circumferential wall of cavity 18.

Alternatively, cavity 18 can be partially enclosed within form-retaining member 10, with only a portion of the circumferential cavity wall of cavity 18 contributed by member 10. In these latter embodiments, channels 12 can be machined into form-retaining member 10, or, depending on the composition of form-retaining member 10, lithographed, engraved, isotropically or anisotropically etched, milled, mechanically or chemically polished, or molded into form-retaining member 10. Alternatively, in these latter embodiments channels 12 can be fabricated on form-retaining member 10 from silicon or resin deposits or slabs.

In embodiments in which cavities 18 are not fully enclosed by inflexible member 10, channels 12 can be rendered fluidly enclosing along cavity 18 by physical attachment to form-retaining member 10 of one or more additional laminae.

Figure 4:
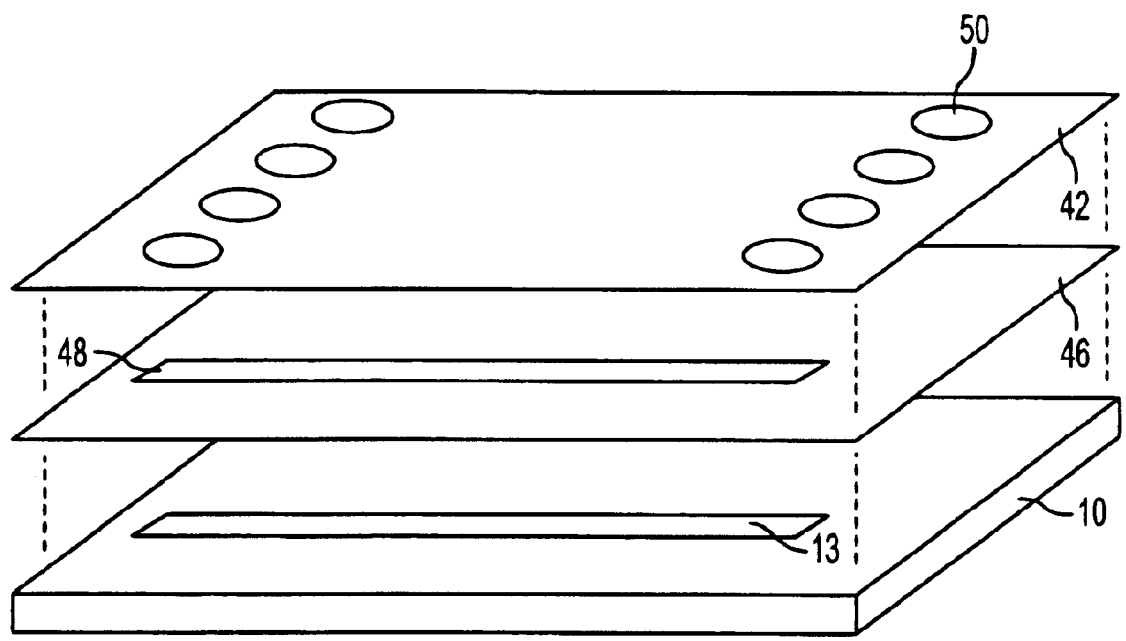
FIG. 4 is an exploded side perspective view of a multilaminate cassette of the present invention.

FIG. 4 is an exploded side perspective view of a multilaminate embodiment of cassette 100 of the present invention.

In the embodiment shown in FIG. 4, form-retaining member 10 includes depression 13. Laminate cover 42 includes a plurality of entries 50. Upon attachment of laminate cover 42 to form-retaining member 10, depression 13 becomes fluidly enclosing along cavity 18, thus completing channel 12, with entries 50 contributing to channel entries 14 and 16.

As with form-retaining member 10, laminate cover 42 can usefully be optically translucent or transparent, and is usefully substantially electrically insulating.

As with form-retaining member 10, laminate cover 42 can be composed of ceramic, quartz, glass, silicon and its derivatives, alumina, polymer, plastic, or mixtures thereof. Among plastics useful in the construction of laminate cover 42 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, polyester, and mixtures and copolymers thereof.

Laminate cover 42 can usefully be, and is often preferably, flexible. Although laminate cover 42 can be of any thickness, to confer flexibility laminate cover 42 can usefully be a film.

Laminate cover 42 can be attached to form-retaining member 10 by bonding means known in the microfabrication arts, including thermal welding, ultrasonic welding, and application of adhesives or adhesive layers.

For example, U.S. Pat. Nos. 5,800,690 and 5,699,157, incorporated herein by reference in their entireties, describe methods for completing channels by attaching planar cover elements to micromachined substrates by thermal bonding, application of adhesives, or by natural adhesion between the two components. U.S. Pat. No. 5,593,838, incorporated herein by reference, teaches that localized application of electric fields permits the meltable attachment of a cover element at about 700° C., well below the flow temperature of silicon (about 1400° C.) or of Corning 7059 glass (about 844° C.). WO 96/04547 (Lockheed Martin Energy Systems), incorporated herein by reference in its entirety, teaches that a cover plate can be bonded directly to a glass substrate after treatment in dilute $NH_4OH/H_2O_2$, followed by annealing at 500° C., well below the flow temperature of silicon-based substrates. WO 98/45693 (Aclara Biosciences), incorporated herein by reference in its entirety, discloses a thermal bonding method for fabricating enclosed microchannel structures in polymeric, particularly plastic, substrates, an adhesive method in which adhesive is applied in a film no more than 2 μm thick, and methods in which fluid curable adhesives are rendered nonflowable by partial curing before apposition of adherends.

Laminate cover 42 is usefully attached to form-retaining member 10 by reversible bonding means, thus permitting the user to separate laminate cover 42 from form-retaining member 10 after completion of electrophoresis, which in turn permits strip 20 to be removed from channel 12 for further processing. Constructing laminate cover 42 as a flexible film offers advantages in such user-mediated separation of laminate cover 42 from form-retaining member 10.

In the embodiment depicted in FIG. 4, laminate cover 42 is attached adhesively to form-retaining member 10 using double-sided laminate adhesive layer 46.

As shown, double-sided laminate adhesive layer 46 has elongate slots 48 that are congruent with depressions 13. Such slots 48 prevent contact between double-sided adhesive layer 46 and strip 20 when strip 20 is movably inserted into channel 12; contact with adhesive can interfere with movable insertion of strip 20 into cassette 100.

In multilaminate embodiments of cassette 100 in which laminate cover 42 is attached with a double-sided adhesive layer 46, the thickness of adhesive layer 46 can be adjusted to change the internal diameter of cavity 18 of channel 12, thus accommodating hydratable strip media of different thicknesses.

In alternative multilaminate embodiments of cassette 100, laminate cover 42 is itself fashioned as a form-retaining member, typically thicker than the flexible film above-described. In some of these embodiments, laminate cover 42 is fashioned as a discrete structure. In other embodiments, form-retaining laminate cover 42 and form-retaining member 10 are movably attached to one other, as by a hinge, or plurality of hinges, present therebetween. The hinge need not itself be fashioned as a separate, intermediating, structure, but can instead be fashioned as a foldable seam between form-retaining member 10 and laminate cover 42. Such seams are common in plastic cases designed to hold, e.g., drill bits.

In cases in which laminate cover 42 is form-retaining, it can be assembled to form-retaining member 10 by, e.g., snapping laminate cover 42 to form-retaining member 10. A pressure compliant surface, on form-retaining member 10 and/or laminate cover 42, facilitates sealing of the two layers, forming an enclosing member suitable for electrophoresis. Although assembly by snapping of laminate cover 42 to form-retaining member 10 has been described with particularity, any other mechanical engagement approach, such as mating of tongue and groove, insertion of a tab into a slot, etc., can also be used to similar effect.

In multilaminate embodiments of cassette 100—both those with flexible and those with form-retaining laminate covers—the internal diameter of cavities 18 can be adjusted by adjusting the depth of incursion of channel 12 into form-retaining member 10. In multilaminate embodiments of cassette 100 in which laminate cover 42 is thicker than a film, the internal diameter of cavities 18 can be adjusted additionally by adjusting the depth of incursion of channel 12 into laminate cover 42.

Channel 12 is so dimensioned—in both multilaminate and unitary embodiments of cassette 100—as to permit insertion of a prior-cast hydratable strip-based electrophoresis medium, such as an IPG strip, in its dehydrated state, and to lodgingly enclose the strip after hydration.

Immobiline DryStrip IPG strips, presently available commercially from Amersham Pharmacia Biotech, (Piscataway, N.J., USA), have an approximate width of 3 mm and a depth of 0.5 mm. Accordingly, to permit electrophoresis of these commercial IPG strips, channel 12 of cassette 100 will have a width of at least about 3.0 mm, 3.1 mm, 3.2 mm, 3.3 mm, 3.4 mm, and even 3.5 mm, 3.6 mm, 3.7 mm, 3.8 mm, 3.9 mm, 4.0 mm, and even 4.1 mm, and will have depth of at least about 0.5 mm, 0.6 mm, 0.61 mm, 0.62 mm, 0.63 mm, 0.64 mm 0.65 mm, 0.66 mm, 0.67 mm, 0.68 mm, 0.69 mm, and even 0.7 mm, 0.71 mm, 0.72 mm, 0.73 mm, 0.74 mm, 0.75 mm, 0.76 mm, and even 0.77 mm so as to movingly engage such strips in their dehydrated state and lodgingly enclose the strips when rehydrated.

ReadyStrip IPG strips, presently available commercially from Bio-Rad (Hercules, Calif., USA) have strip width of 3.3 mm and gel thickness of 0.5 mm. Accordingly, to permit electrophoresis of these commercial IPG strips, channel 12 of cassette 100 will have an approximate width of at least about 3.3 mm, 3.4 mm, and even and even 3.5 mm, 3.6 mm, 3.7 mm, 3.8 mm, 3.9 mm, 4.0 mm, and even 4.1 mm, and will have depth of at least about 0.5 mm, 0.6 mm, 0.61 mm, 0.62 mm, 0.63 mm, 0.64 mm, 0.65 mm, 0.66 mm, 0.67 mm, 0.68 mm, 0.69 mm, and even 0.7 mm, so as to movingly engage such strips in their dehydrated state and lodgingly enclose the strips when rehydrated.

In a presently preferred embodiment, suitable for electrophoresis of strips from both manufacturers, channels 12 have width of 3.7 mm and depth of 0.64 mm.

As would be expected, prior-cast hydratable electrophoretic separation media can, and likely will, be manufactured with dimensions different from those presently used. Accordingly, cassettes 100 of the present invention are not limited to those dimensioned for use with the above-described strips.

Design of the internal dimensions of channel 12, so as to permit insertion of prior-cast hydratable strip based media in their dehydrated state and lodgingly enclose the strips when rehydrated, is well within the skill in the art.

A simple test for suitability of the internal dimensions of channel 12 for a prior-cast hydratable electrophoretic separation medium 20 of any given depth and width is as follows:

(1) Position the cassette horizontally and fill channel 12 with water;

(2) Insert strip 20 through entry 14 or through entry 16 into channel 12 and advance as far as possible by hand;

(3) After 8 hours, bring cassette 100 to the vertical position with the visibly labeled entry superior, and observe.

Dimensions of channel 12 are suitable if, in step (2), strip 20 can be advanced into channel 12 to a point at which less than 1 cm of strip 20 remains outside the entry chosen for insertion, and if, in step (3), air does not directly contact more than 50% of the enclosed separation medium.

At one end of the useable spectrum of channel dimensions, the swelling of the separation medium causes direct, occlusive, contact of the separation medium with the channel's internal wall along substantially all of the channel cavity. In this case, a visibly labeled solution (such as 0.2% w/v bromphenol blue in water) applied to the superior channel entry will be substantially precluded from the channel cavity. That is, a visibly labeled solution will typically not extend more than about 0.25 cm beyond the channel entry into the channel cavity. At the other end of the useable spectrum of channel dimensions, the swelling of the separation medium is insufficient to cause occlusive contact of the separation medium with the channel's internal wall along substantially all of the channel cavity. In this latter case, a visibly labeled solution such as 0.2% w/v bromphenol blue in water will enter the channel cavity from the superior entry when the cassette is brought vertical. In neither case, however, will air contact more than 50% of the enclosed separation medium.

An additional, functional test for suitability of the internal dimensions of channel 12 for a prior-cast hydratable electrophoretic separation medium of given dimensions is to replace step (3) of the test set forth above with an actual electrophoresis experiment; dimensions of channel 12 are suitable if, in step (2), strip 20 can be advanced into channel 12 to a point at which less than 1 cm of strip 20 remains outside the entry chosen for insertion, and if, in step (3), adequate electrophoretic separation is achieved.

If strip 20 is an IPG strip, this latter test can usefully be performed as follows.

Mix 5.0 µL of Serva IEF standard (catalogue no. 39212-01, Serva Electrophoresis GmbH, Heidelberg, Germany) with 120.0 µL of rehydration buffer of the following composition: 8.0 M urea, 0.5% ampholytes (3–10 IPG buffer, cat. no. 17-6001-11, Amersham Pharmacia Biotech), 2.0% (w/v) CHAPS, 20 mM DTT, 0.0025% (w/v) bromphenol blue. Pipette the solution into a channel of the cassette, with the cassette positioned horizontally. Insert the strip into the channel so that about 3 mm overextends the channel entries. Occlude the channel entries with cover tape and allow the strip to rehydrate for 8 hours. Remove cover tape and, if present, loading wells. Contact electrodes to anodic and cathodic ends of the strip. Apply a voltage in three steps according to the following protocol: 250 volts for 15 minutes, ramp from 250–3500 volts for 1 hour and 30 minutes, and 3500 volts for 1 hour. Limit current to 1 mA and power to 4 watts in all three steps. Channel dimensions are suitable if discrete marker bands are observable.

Figure 2:
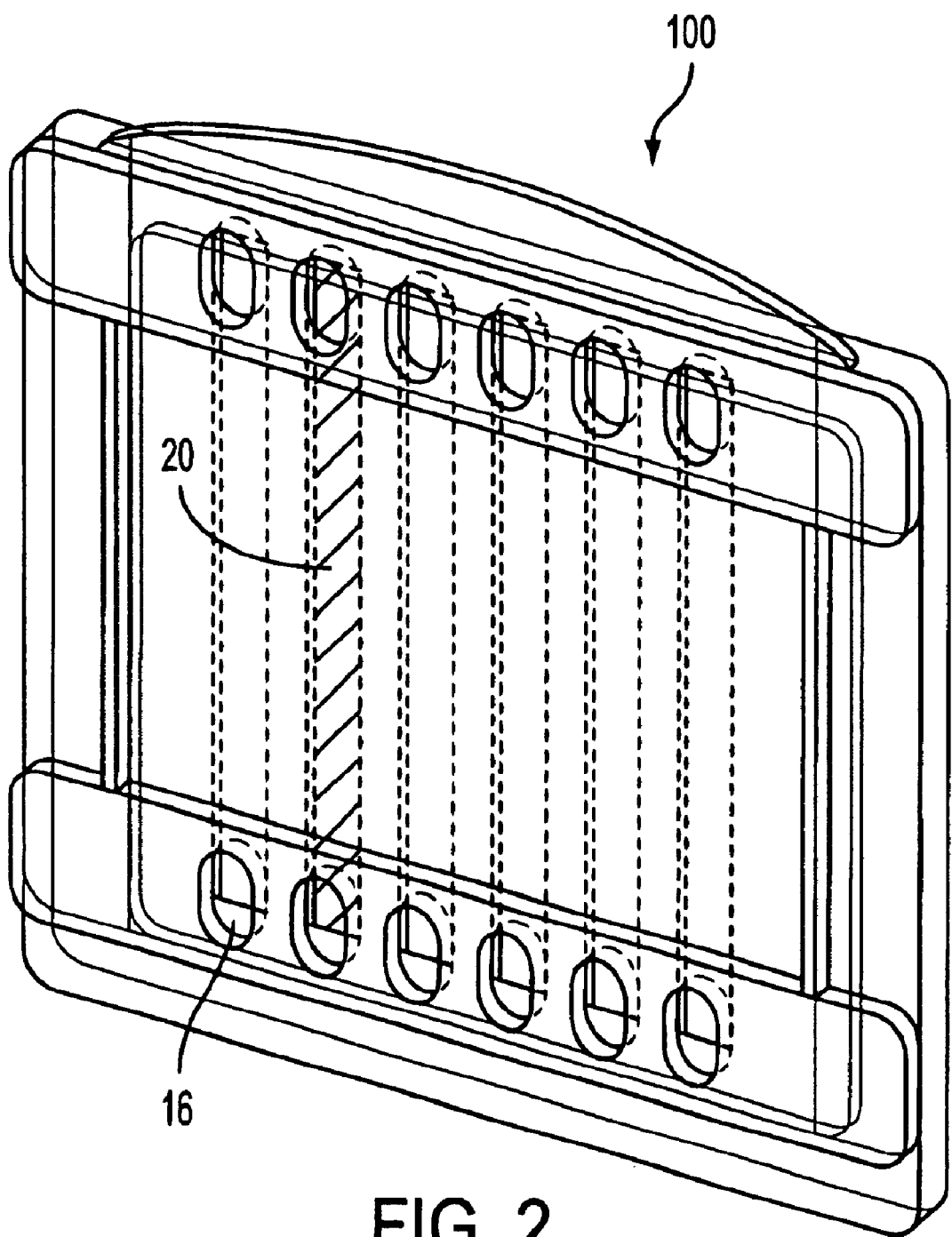
FIG. 2 is a front perspective view of a cassette of the present invention with an IPG strip inserted into one of six available channels.

Channel entries 14 and 16 will typically, but not invariably, be spaced so that channel 12 engages substantially the entire length of strip 20, as shown e.g. in FIG. 2.

IPG strips are currently available commercially in a variety of lengths. For example, Immobiline DryStrip IPG strips, presently commercially available from Amersham Pharmacia Biotech, (Piscataway, N.J., USA), are available with gel lengths of 70 mm, 110 mm, 130 mm, 180 mm, and 240 mm. ReadyStrip IPG strips, presently commercially available from Bio-Rad (Hercules, Calif., USA), are available with gel lengths of 70 mm, 110 and 170 mm.

Thus, in certain presently preferred embodiments of cassette 100 of the present invention, channels 12 are fashioned to accommodate substantially the entire length of strips with gel lengths of 70 mm, 110 mm, 170 mm, 180 mm, and 240 mm in length.

In such commercial IPG strips, the polyester backing typically extends for some distance beyond the gel on either end. Thus, channels 12 will typically have length at least as long as the stated gel length (70, 100, 170, 180, or 240 mm), typically with extension of 1 mm, 2 mm, 3 mm, 4 mm, 5 mm, or even 6 mm on both ends. Thus, for an IPG strip of nominal 70 mm gel length, channel 12 will be at least about 70 mm in length, 72 mm in length, 74 mm in length, 76 mm in length, 78 mm in length, and even 80 or 82 mm in length. In a presently preferred embodiment for IPG strips of 70 mm stated gel length, channel 12 will be 80 mm in length.

It would be expected that rehydratable strip-based separation media will in the future be available in a variety of lengths, just as they are expected to be available in a variety of widths and depths, as described above. It is, therefore, an aspect of the invention to provide cassettes 100 with channels 12 dimensioned to engage prior-cast hydratable electrophoretic separation media of any chosen length.

As suggested above, significant overextension or underextension of channel 12 by strip 20 is undesirable.

For example, if strip 20 extends substantially beyond entry 14, entry 16, or both, the overextending portion(s) of strip 20 will be exposed to atmospheric $CO_2$, obviating an important advantage of the resent invention. Furthermore, the overextending portion(s) of strip 20 can permit leakage of ampholyte and/or protein from the strip. Additionally, only that portion of the separation medium lying between the spaced electrical connections will be functionally available for separation, reducing the functional portion of gel. Finally, the overextending portion(s) might interfere mechanically with establishment of electrical communication properly required for electrophoresis. And when strip 20 underextends channel 12, it can prove difficult to establish effective electrical communication with the enclosed strip.

To accommodate these difficulties in a cassette having channels of nonoptimal length, if strip 20 overextends channel 12, excess can be removed using scissors or knife; typically, only that portion of strip 20 lacking separation media will be so removed. If strip 20 underextends channel 12, the recessed end can be brought into effective electrical communication with the exterior of channel 12 by filling the recessed end with an electrically conductive, channel-filling, material.

Among materials usefully employed to bring the underextended end of strip 20 into electrical communication with an entry 14 or 16 of cassette 100 are materials that can be applied in liquid or semiliquid state, in which state they can conform in shape to the channel interior, and that thereafter polymerize or gel into a shape-holding phase.

Usefully, the material can be a polymer gel, such as agarose. When so used, the agarose can be rendered molten in the presence of electrolyte-containing buffer, such as rehydration solution, applied to entry 14, entry 16, or both as a molten liquid, and thereafter allowed spontaneously to gel with decrease in temperature. Polyacrylamide can also be used, although in this latter case polymerization of monomers and cross-linkers must be effected by addition of catalyst, as is well known in the art.

Usefully, cassette 100 includes a plurality of channels 12. In cases in which cassette 100 includes a plurality of channels 12, the current flow axes of plural channels 12 are usefully substantially parallel to one another, and cavities 18 of plural channels 12 are fluidly noncommunicating with one another except at channel entries 14 and 16.

In such embodiments, channels 12 need not have identical cavity 18 dimensions, a single cassette 100 thus accommodating strips 20 of different dimensions. Typically, however, cavities 18 of plural channels 12 will all have the same internal dimensions.

Although cassette 100 is described above as permitting user-directed insertion of strip 20 into channel 12, it is another aspect of the present invention to provide a cassette, as above-described, in which strips 20 have already been inserted during manufacture. Such cassettes 100 can usefully be disposable.

To facilitate sample application, and in particular to facilitate sample application without cross contamination as among plural channels 12, cassette 100 can usefully include loading wells. FIG. 1 shows one embodiment of such loading wells.

With reference to FIG. 1, cassette 100 is shown to have two well-forming members 22. The two well-forming members define discrete reservoirs, termed loading wells, at each of the six entries 14 and six entries 16, respectively. When cassette 100 is horizontal with well-forming members 22 superior to form-retaining member 10, each loading well can maintain a defined maximum volume of fluid in contact with an entry 14 (or entry 16) without cross-over fluid contact with adjacent entries.

In cases in which sample to be fractionated is applied after insertion of strip 20, the loading wells permit samples of volume less than the maximum reservoir volume to be applied discretely to individual wells 14 (and/or 16) without cross-over contamination. In cases in which sample is applied in rehydration buffer prior to insertion of strips 20 into channels 12, the loading wells prevent cross-over contamination by sample displaced from channel 12 during strip insertion.

Figure 3A:
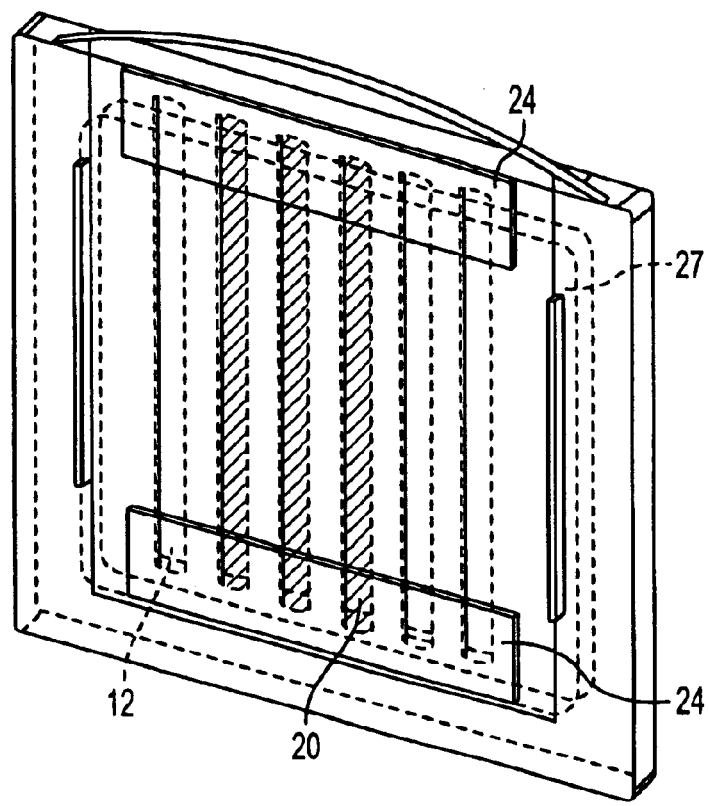
FIG. 3A is a front perspective view of a cassette of the present invention with a first conductive wick contacting the anodic end of IPG strips present in three of six available channels and a second conductive wick contacting the cathodic end of the three IPG strips.
Figure 3B:
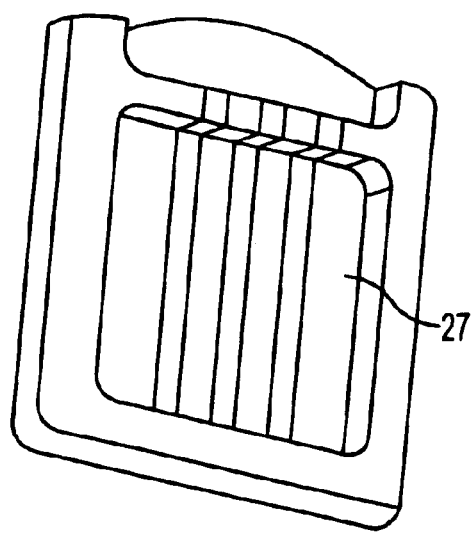
FIG. 3B is a back perspective view of a cassette of the present invention, particularly showing a recessed region that facilitates heat dissipation during electrophoresis.

After sample to be fractionated (such as a protein sample for isoelectric focusing on IPG strips) enters the separation medium of strip 20, cross-over contamination among channels 12 is usually foreclosed, even if entries 14 are thereafter placed in fluid communication with one another and entries 16 are thereafter placed in fluid communication with one another. Accordingly, well-forming members 22 can be removable. Such removal can facilitate subsequent application of conductive wicks 24, as shown in FIG. 3A and further described below.

Because well-forming member 22 is typically removed prior to electrophoresis, there are fewer constraints on the materials from which it can be constructed than for form-retaining member 10 and, in multilaminate embodiments of cassette 100, for laminate cover 42. Indeed, well-forming member 22 can be constructed of any material that is substantially chemically unreactive with the rehydration solution, such as ceramic, quartz, glass, silicon and its derivatives, plastic, natural or synthetic rubber polymers, or mixtures thereof. Among plastics useful in the construction of well-forming member 22 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, and mixtures thereof. Silicone and its derivatives are also useful.

In certain embodiments, well-forming member 22 can be composed of electrically conductive materials; this facilitates "active rehydration" of strip 20. In "active rehydration", strip 20 is rehydrated in the presence of a low voltage gradient, approximately 100 V, established along the channel current flow axis of strip 20 between entries 14 and 16.

In cases in which active rehydration is desired, well-forming member 22 can be composed of an electrically-conductive material, such as an electrically-conductive polymer, such as a polymer impregnated or doped with carbon. After both strip 20 and rehydration solution are applied to channel 12 (in either order), a cathode is contacted to first conductive well-forming member 22 and an anode is contacted to second conductive well-forming member 22 and a voltage applied during the rehydration period. The anode and cathode can be, e.g., an electrode bar, such as is found on the MultiPhor (Amersham Pharmacia Biotech, Piscataway, N.J.) or Blue Horizon (Serva, Heidelberg, Germany) devices.

When cassette 100 is unitary—that is, having channels 12 formed completely within form-retaining member 10—well-forming members 22 can be attached to form-retaining member 10. When cassette 100 is, instead, multilaminate—e.g., with channels 12 formed in part by a laminate cover 42—well-forming members 22 can be attached to laminate cover 42, as shown in FIG. 5.

Figure 5:
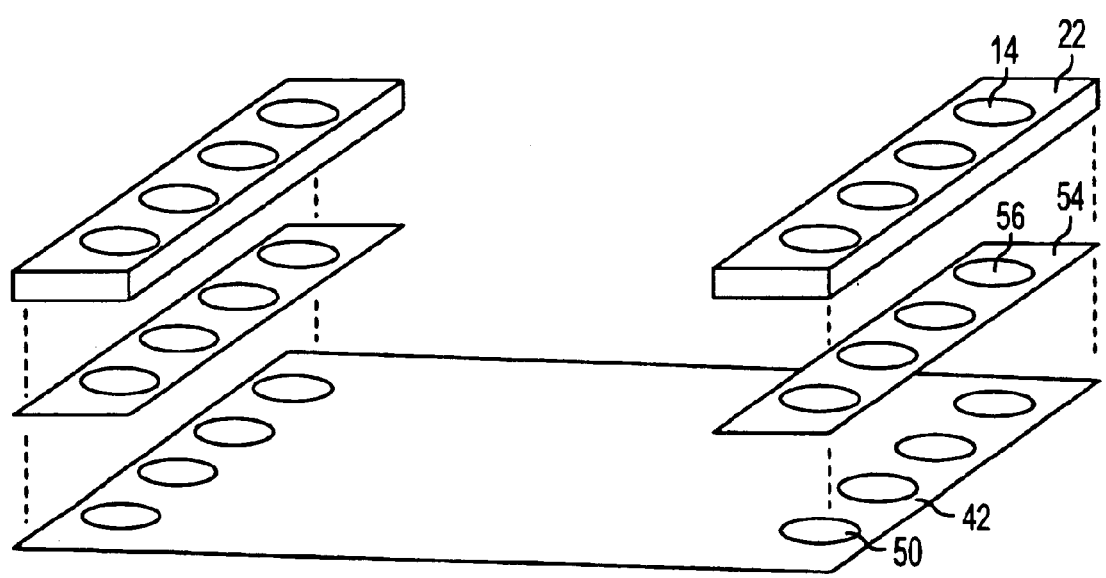
FIG. 5 is an exploded side perspective view of a loading well assembly of a cassette of the present invention.

FIG. 5 is an exploded side perspective view showing well-forming members 22 attached adhesively to laminate cover 42 using double-sided well-forming member adhesive layer 54. However, as described above with respect to attachment of laminate cover 42 to form-retaining member 10, which discussion is incorporated herein by reference, well-forming member 22 can be attached to laminate cover 42 by a variety of bonding means well known in the microfabrication arts, including thermal welding, ultrasonic welding, and application of liquid or partially cured adhesives, as well as by means of adhesive layers.

Well-forming member 22 can in the alternative be attached to laminate cover 42 by engagement of opposing, matching surfaces, as in a snap, or engagement of tongue with groove, or engagement of tab with slot.

However bonded, well forming members 22 will usefully be reversibly attached to cassette 100, thus permitting removal of the well-forming members prior to electrophoresis. In cases in which attachment is by means of a double-sided well-forming member adhesive layer 54, the adhesive layer is usefully designed to adhere more strongly to form-retaining member 10 (or, in multilaminate embodiments, to laminate cover 42) than to well-forming member 22; in such adhesively biased embodiments, removal of well-forming member 22 will typically leave adhesive layer 54 on form-retaining member 10 (or laminate cover 42), facilitating application of conductive wicks, as further described below.

Although cross-contamination of samples as among plural channels 12 will typically be foreclosed by entry of sample into the separation medium of strip 20, thus obviating the requirement for continued presence of well-forming members 22 during electrophoresis, it can nonetheless be advantageous further to seal entries 14 and/or 16 after sample application.

In these latter embodiments, sealing is accomplished by application to entries 14 and/or 16 of a material that is electrically conductive, that can be applied in a state in which it conforms in shape to the entry and/or loading well, and that thereafter polymerizes or gels into a shape-holding phase. As above, such material can usefully be a polymer gel, such as agarose or acrylamide.

In particularly useful approaches, entries 14 and/or 16 are sealed with an amount of material sufficient to fill channel 12 and entry 14 (and/or entry 16) to a level flush with the surface of form-retaining member 10. Such geometry facilitates electrical contact of the anodic and cathodic ends of strip 20 directly or indirectly with anode and cathode electrodes.

Returning to FIG. 1, cassette 100 can optionally, and usefully, include ribs 40.

Ribs 40 facilitate alignment of laminate cover 42 and well-forming members 22 during manufacture of cassette 100. Ribs 40 can also facilitate proper operational engagement of cassette 100 by an electrophoresis chamber or buffer core, as further described below.

Ribs 40 can be machined or molded directly from form-retaining member 10, or can be separately constructed and fixed thereto. When separately constructed, ribs 40 are usefully constructed of solid or semisolid materials that are readily machined, molded, or etched, and that are chemically compatible—that is, do not suffer substantial degradation upon contact—with electrophoretic buffer systems. Usefully, ribs 40 can be constructed of materials that are substantially electrically insulating, including ceramic, quartz, glass, silicon and its derivatives, or plastic, or mixtures thereof. Among plastics useful in the construction of ribs 40 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, polyester, and mixtures and copolymers thereof.

As noted above, after rehydration of and introduction of sample into strip 20, strip 20 becomes lodgingly enclosed in cavity 18 of channel 12. With strip 20 so enclosed, electrophoresis can then be performed, without removing strip 20 from cassette 100, by applying a voltage gradient to flow current through strip 20 along the channel current flow axis sufficient to effect electrophoretic separation of analytes therein.

FIG. 3A illustrates one useful, but nonlimiting, approach by which cassette-enclosed strip 20 is rendered contactable by cathode and anode electrodes to complete the necessary electrical circuit.

FIG. 3A is a front perspective view of a cassette of the present invention having six channels 12. As shown, a first conductive wick 24 contacts strips 20 (present in three of six available channels 12) at entries 14; a second conductive wick 24 contacts strips 20 at entries 16.

Wick 24 includes an electrically conductive material. The material need not be constitutively conductive: it suffices, and indeed typically will be the case, that wick 24 is conductive when wet. In this latter case, wick 24 can usefully be composed of a bibulous material, such as paper, nitrocellulose, felt, nylon, or derivatives thereof.

As described above, as an alternative or in addition to the presence of wicks 24, strip 20 can be electrically coupled to cathode and anode electrodes through intermediation of electrically conductive polymers such as agarose.

As shown in FIG. 3A, first conductive wick 24 can usefully contact each of plural entries 14, and second conductive wick 24 can usefully contact each of plural entries 16, facilitating application of current in parallel to plural channels 12. While useful, such geometry is not required.

First conductive wick 24 is then contacted with an electrode, serving as either cathode or anode. The choice as between applying a cathode or anode to wick 24 depends upon the intended electrophoretic technique, the location of sample application, and other conditions well known to those in the electrophoretic arts. For example, for isoelectric focusing using IPG strips, where one end of the strip is acidic and the other basic, the basic end of the strip is preferably placed in electrical communication with the cathodic electrode.

Second conductive wick 24 is then contacted with an electrode (an anode if first wick 24 is contacted with the cathode, a cathode if first wick 24 is contacted with the anode).

Any means of electrode attachment to wicks 24 can be used, as long as effective electrical communication is established.

In an alternative to use of conductive wicks 24, spaced electrical communication with enclosed strip 20 can be effected by direct contact of strip 20 with anode and cathode electrodes. Contact can be accomplished by passage of anode and cathode electrodes through entries 14 or 16, or alternatively by passage of electrodes through form-retaining member 10 or laminate cover 42 elsewhere than at entries 14 and/or 16. As an example of the latter approach, electrodes shaped as blades can be used to pierce laminate cover 42 in embodiments in which laminate cover 42 is a flexible film, thereby contacting enclosed strip 20 at spaced intervals.

Electrophoresis can thereafter be conducted with cassette 100 in any physical orientation. In a particularly useful approach, electrode contact is effected using an adaptor that permits electrophoresis to be conducted with cassette 100 maintained vertically; as noted above, even when cassette 100 is held vertical, channels 12 of cassette 100 can be horizontal or vertical, as desired.

Returning to FIG. 3A, it is, therefore, another aspect of the invention to provide an adaptor that permits cassettes 100 of the present invention, within which are lodgingly enclosed strips 20, to be electrophoresed in a vertical direction. It should be noted that even when cassette 100 is itself oriented vertically, channels 12 can still be oriented horizontally; in such an orientation, channels 12 of cassette 100, if present plurally, would be spaced with vertical offset from one another. For clarity, therefore, the term "vertical" is intended t refer to the orientation of the cassette, not the channels.

Electrophoresis of cassette 100 in the vertical dimension has the significant advantage of reducing the bench footprint of the electrophoresis device, freeing up valuable bench space for other equipment or uses.

Furthermore, modular electrophoresis systems for performing slab gel electrophoresis in the vertical dimension are well known, see e.g. U.S. Pat. Nos. 5,888,369 and 6,001,233, and are commercially available (Invitrogen, Carlsbad, Calif., USA; Bio-Rad, Hercules, Calif., USA). In preferred embodiments, the adaptor of the present invention permits cassettes 100 of the present invention to be electrophoresed in such existing modular electrophoresis systems, permitting the efficient use of such prior-purchased equipment for electrophoresis of prior-cast hydratable electrophoretic separation media, such as IPG strips.

Figure 6A:
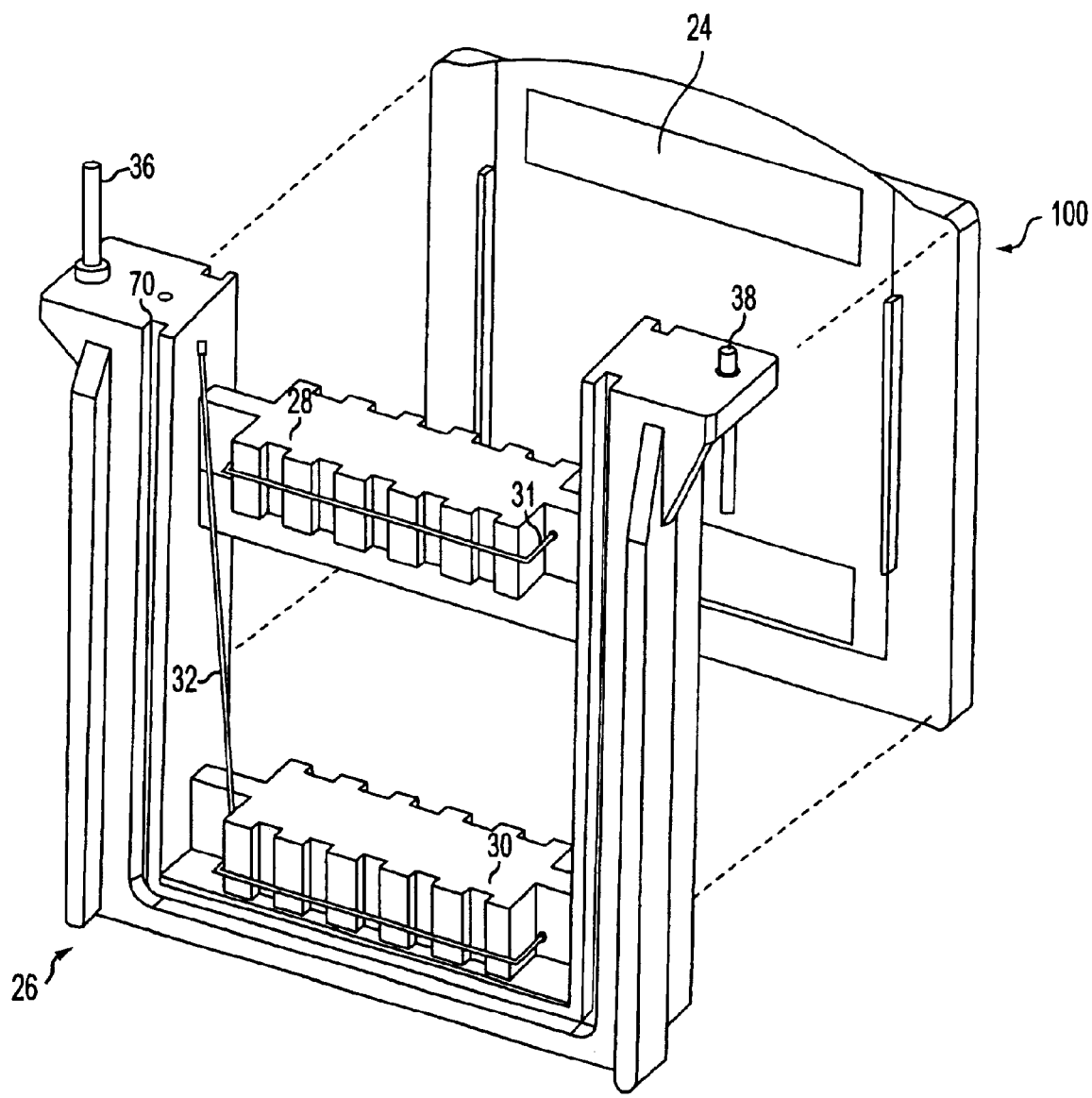
FIG. 6A is a front perspective view of a buffer core of the present invention (front) operationally aligned to contact its anode and cathode electrodes respectively to anodic and cathodic wicks of a cassette of the present invention (rear)
Figure 6B:
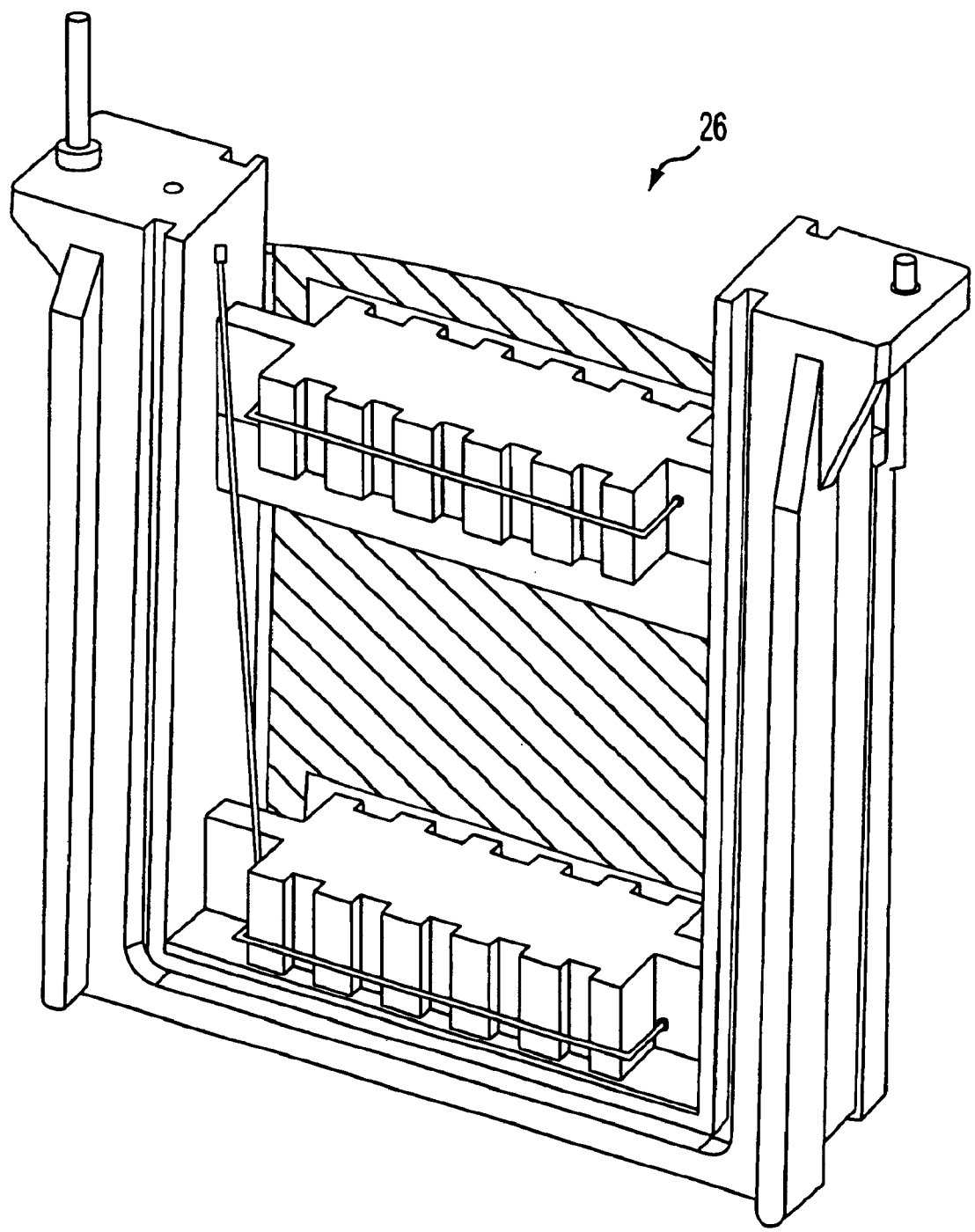
FIG. 6B is a front perspective view of the buffer core and cassette of FIG. 6A in operational contact with one another.
Figure 6C:
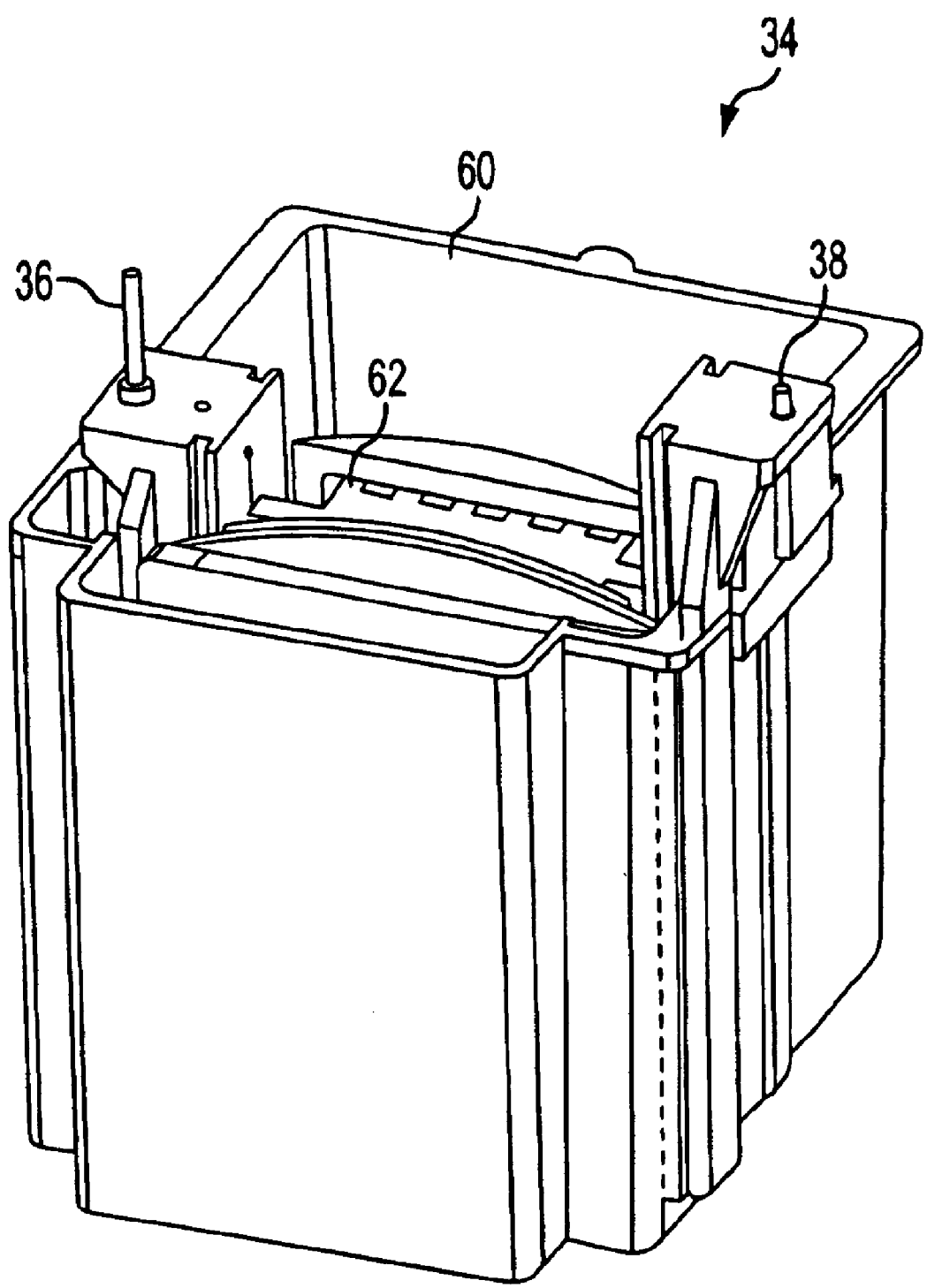
FIG. 6C shows a buffer core of the present invention, with cassettes of the present invention operationally engaged thereupon, further engaged in an electrophoresis chamber.

FIG. 6A is a front perspective view of an adaptor, termed a buffer core, of the present invention (front) operationally aligned with, but not yet contacting, a cassette of the present invention (rear); operational contact is shown in FIG. 6B. As can be seen, buffer core 26 is designed simultaneously to align cathode electrode wire 31 with cathodic wick 24 of cassette 100 and anode electrode wire 32 with anodic wick 24 of cassette 100

In the embodiment shown, cathode wire 31 is attached at a first end to cathode contact prong 38; analogously, anode wire 32 is attached at a first end to anode contact prong 36. Contact prongs 38 and 36 permit the removable attachment of wires having standard female gender plugs; as is well known in the electrophoresis arts, the other end of such wires is typically connected to a regulatable power supply.

Also as shown, cathode wire 31 extends from cathode contact prong 38 to serrated support ridge 28 before terminating at a second end, and anode wire 32 extends from anode contact prong 36 to serrated support ridge 30 before terminating at a second end. Contact between anode wire, cathode wire, and their respective wicks 24 of the cassettes of the present invention is effected, in the embodiment shown, across the serrated support ridge, which ridge facilitates tight contact as between electrode wire and conductive wick. In such embodiments, serrated support ridges 28 and 30 are typically composed of materials that are substantially electrically insulating and substantially inert to electrophoresis running buffers, for example, of plastic.

Although not shown in either FIG. 6A or FIG. 6B, buffer core 26 can, and typically will, be operationally aligned and contacted simultaneously with a second cassette 100, which in FIG. 6A and FIG. 6B would be positioned further in front of buffer core 26. So aligned and so contacted, buffer core 26 and cassettes 100 define an internal chamber 62, open only at the top, and sealed, except from above, from external liquids. If the number of strips needed to be electrophoresed can be accommodated in a single cassette, a "buffer dam", dimensioned similarly to cassette 100 but lacking channels 12, can be used to complete buffer core internal chamber 62.

In order to conduct electrophoresis using cassettes and buffer cores of the present invention, cassettes 100 (or singular cassette 100 and a buffer dam) are aligned and contacted to buffer core 26. The assembly is then engaged in electrophoresis buffer chamber 34 which itself, or in conjunction with an additional device, urges cassettes 100 (and/or buffer dam) into sealable contact with buffer core 26. Such additional urging device can be a cam-activated clamp, as further described in U.S. Pat. No. 6,001,233, incorporated herein by reference in its entirety. Alternatively, buffer core 26 is first loosely engaged in electrophoresis buffer chamber 34, and cassettes thereafter aligned, contacted to, and then further urged against buffer core 26.

Fluid-tight contact between buffer core 26 and cassette 100 (and/or buffer dam) is typically, but optionally, further facilitated by a gasket, such as a silicone gasket, fitted into groove 70 of buffer core 26.

As noted above, buffer core 26 and cassettes 100 (or singular cassette 100 and a buffer dam) in sealed engagement therewith define internal chamber 62. This chamber isolates cathode wire 31 and anode wire 32 from fluids present external to buffer core 26 in electrophoresis chamber 34 (chamber 60), so long as the fluid level in electrophoresis chamber 60 does not over top cassettes 100.

Accordingly, electrophoresis chamber 34 can be filled with any chosen liquid solution, to a level that does not overtop cassettes 100, without affecting the electrical circuit. Such fluids can thus usefully serve as a heat sink, reducing the temperature of strips 20 as they are subjected to current flow in cassettes 100.

Electrophoresis is conducted by attaching, via contact prongs 36 and 38, anode and cathode to a regulatable power supply, and applying a voltage gradient sufficient to flow a current through strip 20, the voltage gradient being sufficient to effect separation of analytes within the separation medium of strip 20. In cases in which strip 20 is an IPG strip, proteins, influenced by the voltage gradient, begin to migrate until the pI of the protein coincides with the pH on the immobilized gradient, at which point the focused protein ceases to move.

Upon completion of electrophoresis, strips 20 can be withdrawn from cavity 18 for further processing. As described earlier, although strips 20 can at times be removed upon drying via channel entries 14 and 16, strips 20 will typically be removed by expanding the dimensions of cavity 18 of channel 12; in multilaminate embodiments of cassette 100, this is accomplished by separating laminate cover 42 from form-retaining member 10.

The buffer core embodiment above-described is designed to facilitate electrophoresis of a cassette in which, for each channel present therein, channel entries 14 and 16 permit electrical communication with the channel cavity 18 therebetween through a common surface of cassette 100, as is shown, e.g., in FIGS. 1–3.

Such a geometry is not required, however. The invention thus further provides a cassette in which entries 14 and 16 do not open through the same surface of form-retaining member 10, and a buffer core suited to electrophoresis of such a cassette. A principal advantage of such a geometry is that it can render the cassette compatible with buffer cores presently sold for slab gel SDS-polyacrylamide gel electrophoresis.

Figure 7A:
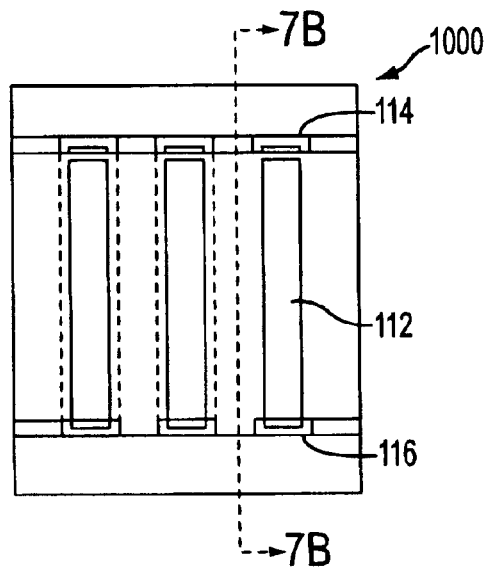
FIG. 7A is a front view of a cassette of the present invention in which channel entries open through opposite surfaces of the cassette.
Figure 7B:
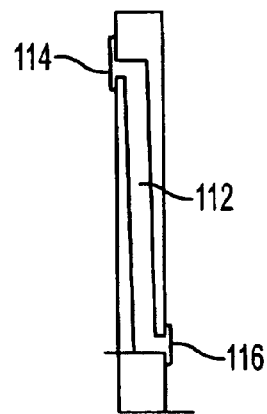
FIG. 7B is a side view of the cassette of FIG. 7A.

FIG. 7A is a front view, and FIG. 7B a side view, of a cassette 1000 of the present invention in which entries 114 and 116 of channels 112 respectively open through opposite surfaces of cassette 1000.

Channels 112 of cassette 1000, like channels 12 of cassette 100, are so dimensioned as to movingly engage a prior-cast hydratable electrophoretic separation medium in its dehydrated state and lodgingly enclose the strip after rehydration.

As should be apparent, in order to conduct electrophoresis using cassette 1000 as the enclosing member, cathode and anode must establish electrical communication with strip 20 from opposite sides of cassette 1000.

As when entries 14 and 16 open channel 12 to the same face of cassette 100, so too electrical communication of channel 112 through entries 114 and 116 can be direct, as by through-passage of electrodes through respective entries, or indirect, as by intermediation by polymer gels and/or conductive wicks. Additionally, however, when entries 114 and 116 open on opposite sides of cassette 1000, electrical communication can be established by contact of anode and cathode electrodes separately to a first and a second buffer reservoir, which reservoirs in turn separately contact entries 114 and 116.

In the latter case, first and second buffer reservoirs must be maintained in electrical isolation from one another, except by way of a circuit to be completed through the separation medium of strip 20.

Such geometry can readily be effected by sealingly contacting cassettes 1000, or a singular cassette 1000 and a buffer dam, to a buffer core 126, as further described in commonly-owned U.S. Pat. No. 5,888,369, incorporated herein by reference in its entirety, and as available commercially from Invitrogen Corp. (XCell II™ Buffer Core with Electrodes, catalogue no. EI9014X, Invitrogen Corp., Carlsbad, Calif.).

Figure 7C:
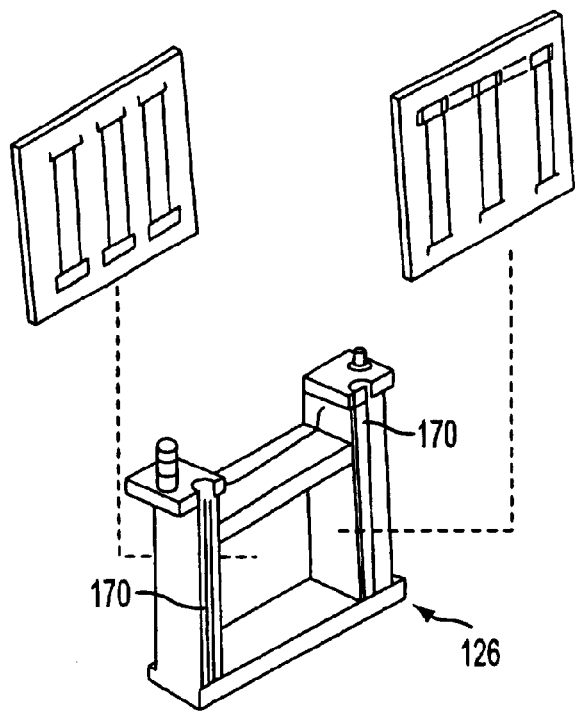
FIG. 7C is an exploded perspective view of two cassettes as shown in FIGS. 7A and 7B showing their operational relationship to a prior art buffer core.
Figure 7D:
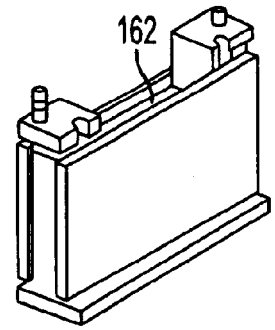
FIG. 7D is a perspective view of the cassettes of FIGS. 7A and 7B in operational contact with a prior art buffer core.

In order to conduct electrophoresis using such system, two cassettes 1000 (or a single cassette 1000 and a buffer dam) are lodgingly engaged in operational alignment with buffer core 126, as shown in FIGS. 7C and 7D.

The assembly of buffer core and cassettes is then engaged in electrophoresis buffer chamber 34 which itself, or in conjunction with an additional device, urges cassettes 1000 (and/or buffer dam) into sealable contact with buffer core 126. Such additional device can usefully be a cam-activated clamp, such as that further described in U.S. Pat. No. 6,001,233, incorporated herein by reference in its entirety. Alternatively, buffer core 126 is first loosely engaged in electrophoresis buffer chamber 34, and cassettes thereafter aligned, contacted to, and then further urged against buffer core 126.

Fluid-tight contact between buffer core 126 and cassette 1000 (and/or buffer dam) is typically, but optionally, further facilitated by a gasket, such as a silicone gasket, fitted into groove 170 of buffer core 126.

Buffer core 126 and cassettes 1000 (or singular cassette 1000 and buffer dam) in sealed engagement therewith define internal chamber 162 which, if cassettes 1000 are not overtopped, is fluidly noncommunicating with electrophoresis buffer chamber 34. A conductive solution is then added to internal chamber 162 to a level that (i) contacts cassette entries 114 (or 116, as the case may be) that open into chamber 162, and (ii) that does not overtop cassettes 1000. A conductive solution is also added to electrophoresis buffer chamber 34 to a level that (i) contacts the cassette entries 116 (or 114, as the case may be) that open into chamber 34, and (ii) that does not overtop cassettes 1000.

As further described in commonly-owned U.S. Pat. No. 5,888,369, and well known to users of the XCell™ Sure-Lock system, the electrode geometry of buffer core 126 effects contact of the anode to internal chamber 126 and cathode to an external reservoir 60 formed in chamber 34, thus permitting the requisite voltage gradient to be applied across strip 20 to effect electrophoresis.

It should be noted that a potential disadvantage of direct contact of channels 112 and strips 20 with liquid reservoirs is the increased likelihood of ampholyte and/or sample leakage from the separation medium.

Although the cassettes of the present invention have been particularly described herein above as having at least one prior-formed channel with sufficient dimensional integrity as to permit the lodging by hydration of prior-cast hydratable separation media engaged there within, prior-formed channels are only one approach to hydratingly lodging such media within an enclosing member.

By way of example only, the enclosing member, if malleable yet shape-retaining, can be wrapped around the strip in its dehydrated form, fashioning a de novo channel which, upon hydration of the strip, lodgingly encloses the rehydrated strip there within.

In a further aspect, the present invention provides kits that facilitate the practice of the methods of the present invention.

The kits of the present invention comprise at least one enclosing member (cassette) of the present invention, and, as convenient, further comprise at least one of prior-cast hydratable electrophoretic separation media, conductive wicks, containerized buffers—either in liquid form, at use (1x) concentration or higher concentration for further dilution, or in dry form to be reconstituted with water of suitable quality—buffer cores, and electrophoresis buffer tanks.

EXAMPLE 1

Determination of Channel Tolerances

Three cassettes were manufactured by machining six parallel channels each into form-retaining plastic slabs, with geometry essentially as shown in FIG. 1. The six channels of the first cassette all were 0.77 mm in depth, with two channels 4.09 mm in width, two channels 0.65 mm in width, and two channels 3.35 mm in width. The six channels of the second cassette all were 0.65 mm in depth, with two channels 4.09 mm in width, two channels 0.65 mm in width, and two channels 3.35 mm in width. The six channels of the third cassette all were 0.57 mm in depth, with two channels 4.09 mm in width, two channels 0.65 mm in width, and two channels 3.35 mm in width. The channels were rendered fluidly enclosing except at terminal entries by application of a flexible laminate cover to each of the three cassettes.

Serva IEF standard, 5 µL, (catalogue no. 39212-01, Serva Electrophoresis GmbH, Heidelberg, Germany) was mixed with 120 µL of rehydration buffer of the following composition: 8.0 M urea, 0.5% ampholytes (3–10 IPG buffer, cat. no. 17-6001-11, Amersham Pharmacia Biotech), 2.0% (w/v) CHAPS, 20 mM DTT, 0.0025% (w/v) bromphenol blue. The solution was pipetted into each channel of the three cassettes, with the cassette positioned horizontally.

An Immobiline DryStrip 3–10 7 cm gel (Amersham Pharmacia Biotech, Piscataway, N.J., USA) was inserted into each channel. The channel entries were occluded with cover tape and the strips allowed to rehydrate for 8 hours. Cover tape was removed, as were loading wells if present.

A filter paper wick dampened with water was placed in contact with the extreme ends of the gel portion of the strip at the terminal entries.

Electrodes were contacted to the wick at the anodic and cathodic ends of the cassette and a voltage applied in three steps according to the following protocol: 250 volts for 15 minutes, ramp from 250–3500 volts for 1 hour and 30 minutes, and 3500 volts for 1 hour. Current was limited to 1 mA and power to 4 watts in all three steps.

Strips were removed, stained with Coommasie blue stain, aligned, and photographed.

Figure 8:
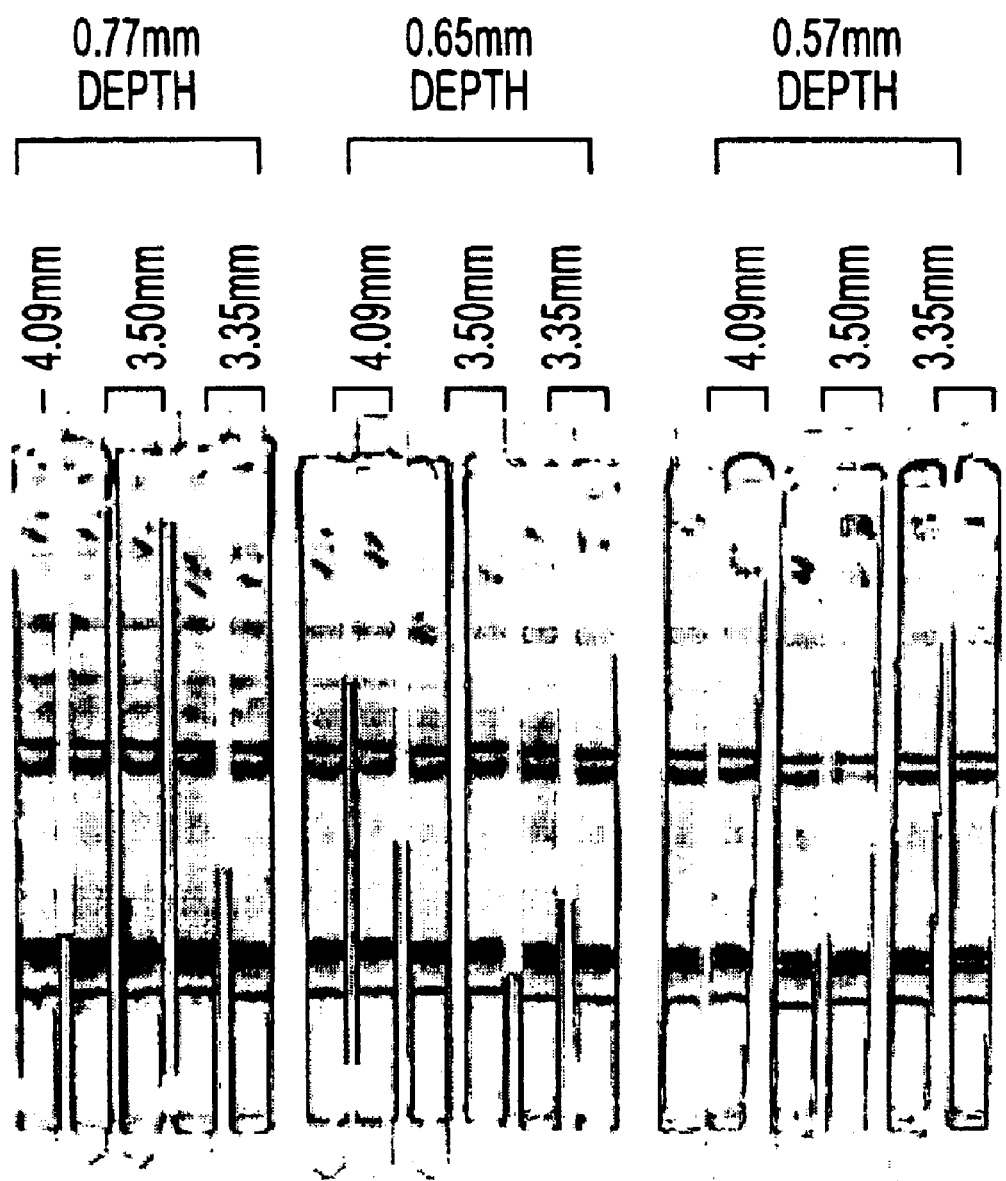
FIG. 8 shows IPG strips after electrophoresis in channels of the stated internal dimensions.

Results shown in FIG. 8 indicate that even the largest channel, 4.09 mm in width and 0.77 mm in depth, permitted adequate focusing of the Serva IEF standard (left-most lane) in strips with nominal width of 3 mm and depth of 0.5 mm.

All patents and publications cited in this specification are herein incorporated by reference as if each had specifically and individually been incorporated by reference herein. Although the foregoing invention has been described in some detail by way of illustration and example, it will be readily apparent to those of ordinary skill in the art, in light of the teachings herein, that certain changes and modifications may be made thereto without departing from the spirit or scope of the appended claims, which, along with their full range of equivalents, alone define the scope of invention.

What is claimed is:

1. A method for performing electrophoresis, comprising: hydratingly lodging a prior-cast hydratable electrophoretic separation medium within an enclosing member, the enclosing member comprising a plurality of channels, each channel comprising a first channel entry and a second channel entry, wherein the entries permit spaced electrical communication with said enclosed medium and at least one of the entries is dimensioned to allow insertion therethrough of the prior-cast hydratable electrophoretic separation medium in its dehydrated state into the enclosing member, wherein the medium comprises an immobilized pH gradient; and then using said spaced electrical communication to establish a voltage gradient in said medium sufficient to effect electrophoretic separation of analytes therein.

2. The method of claim 1, further comprising the antecedent step of inserting said prior-cast hydratable electrophoretic separation medium in its dehydrated state within said enclosing member.

3. The method of claim 2, wherein said step of hydratingly lodging comprises:

contacting said enclosed dehydrated prior-cast hydratable electrophoretic separation medium with an aqueous solution for a time sufficient to lodge said separation medium within said enclosing member.

4. The method of claim 3, wherein said aqueous solution comprises a sample to be separated in said prior-cast hydratable separation medium.

5. The method of claim 1, further comprising a later step of removing said prior-cast hydratable electrophoretic separation medium from said enclosing member.

6. A cassette for performing electrophoresis, comprising:

means for hydratingly lodging a plurality of prior-cast electrophoretic separation media within an assembled enclosing member; and means for spaced electrical communication with at least one of the plurality of enclosed media, wherein said spaced electrical communication means can be used to establish a voltage gradient in at least one of the plurality of enclosed separation media sufficient to effect electrophoretic separation of analytes therein, said assembled enclosing member permits insertion therein of the plurality of prior-cast hydratable electrophoretic separation media in its dehydrated state, and said means for hydratingly lodging comprises means for separately enclosing each of the plurality of media therein.

7. A cassette for performing electrophoresis, comprising:

a form-retaining member; and at least one channel, wherein said form-retaining member imparts dimensional integrity to said at least one channel;

said at least one channel has a first channel entry, a second channel entry, and a cavity therebetween, at least one of said channel entries being so dimensioned as to permit insertion of a hydratable prior-cast electrophoretic separation medium in its dehydrated state therethrough into said channel cavity, said channel cavity being so dimensioned as to lodgingly enclose said hydratable prior-cast electrophoretic separation medium in its rehydrated state, said first and second channel entries permit spaced electrical communication with said channel cavity, and said cassette comprises a plurality of said channels.

8. The cassette of claim 7, wherein said form-retaining member contributes the entire circumferential wall of the cavity of each of said at least one channel.

9. The cassette of claim 7, further comprising:
a laminate cover,
wherein said laminate cover adheres directly or indirectly to said form-retaining member and contributes at least part of the circumferential wall of each of said at least one channels.

10. The cassette of claim 9, wherein adherence of said laminate cover to said form-retaining member is reversible.

11. The cassette of claim 7, wherein, for each of said at least one channel, said first and second channel entries permit electrical communication with the cavity therebetween through a common surface of said cassette.

12. A kit for electrophoresing prior-cast hydratable electrophoretic separation media, comprising:
a cassette according to claim 7; and
at least one prior-cast hydratable electrophoretic separation medium suitably dimensioned as to be hydratingly lodgeable in said cassette.

13. A kit for electrophoresing prior-cast hydratable electrophoretic separation media, comprising:
a cassette according to claim 7; and
at least one conductive wick.

14. A cassette for performing electrophoresis, comprising:
a first well-forming member,
a form-retaining member; and
at least one channel,
wherein
said form-retaining member imparts dimensional integrity to said at least one channel;
said at least one channel has a first channel entry, a second channel entry, and a cavity therebetween, said channel cavity being so dimensioned as to permit insertion of a hydratable prior-cast electrophoretic separation medium in its dehydrated state and lodgingly enclose said hydratable prior-cast electrophoretic separation medium in its rehydrated state;
said first and second channel entries permit spaced electrical communication with said channel cavity; and
said first well-forming member adheres, directly or indirectly, to said form-retaining member and defines a separate fluid reservoir at the first channel entry of each of said at least one channel.

15. The cassette of claim 14, further comprising:
a second well-forming member,
wherein said second well-forming member adheres, directly or indirectly, to said form-retaining member and defines a separate fluid reservoir at the second channel entry of each of said at least one channel.

16. The cassette of claim 15 wherein adherence of said well-forming members to said form-retaining member is reversible.

17. A cassette for performing electrophoresis comprising:
a form-retaining member; and
at least one channel,
wherein
said form-retaining member imparts dimensional integrity to said at least one channel;
said at least one channel has a first channel entry, a second channel entry, and a cavity therebetween, said channel cavity being so dimensioned as to permit insertion of a hydratable prior-cast electrophoretic separation medium in its dehydrated state and lodgingly enclose said hydratable prior-cast electrophoretic separation medium in its rehydrated state;
said first and second channel entries permit spaced electrical communication with said channel cavity;
for each of said at least one channel, said first and second channel entries permit electrical communication with the cavity therebetween through separate surfaces of said cassette; and
said cassette comprises a plurality of said channels.

18. The cassette of any of claims 7 and 8–15, further comprising:
at least one prior-cast hydratable electrophoretic separation medium,
wherein each of said at least one prior-cast separation medium is engaged in a separate channel of said cassette.

19. The cassette of claim 7 or 17, wherein the at least one of the plurality of channels has a width of 3.0 mm to 4.1 mm.

20. A buffer core for vertical electrophoresis of prior-cast hydratable separation media, comprising:
a substantially inflexible frame, said frame having a first cassette engagement face;
an anode; and
a cathode,
wherein said anode and cathode are positioned to effect simultaneous spaced contact with a common surface of a cassette operationally contacted to said first cassette engagement face.

21. A buffer core according to claim 20, further comprising:
a second cassette engagement face;
wherein operational engagement of a first and second cassette respectively to said first and second frame engagement faces creates a chamber internal to said frame that is sealed on 5 sides;
wherein said cathode and said anode are each in electrical communication with the interior of said internal chamber; and
wherein operational contact of a first and second cassette to said respective first and second frame engagement faces causes spaced contact of said anode and said cathode to a common surface of at least one of said cassettes.

22. A method for performing electrophoresis, comprising:
engaging a first cassette in operational contact with the first engagement face of a buffer core according to claim 20, wherein the first cassette encloses at least one electrophoretic separation medium and permits spaced electrical communication with each of the enclosed media; and
establishing a voltage gradient in the enclosed media sufficient to effect electrophoretic separation of analytes within each of the media.

23. The method of claim 22, wherein the separation media are prior-cast hydratable media strips.

24. The method of claim 23, further comprising the antecedent step of hydratingly lodging said media strips within the first cassette.

25. The method of claim 24, wherein the step of hydratingly lodging said media strips comprises:
  inserting at least one prior-cast hydratable media strip in its dehydrated state within the first cassette; and
  contacting the at least one dehydrated media strip with an aqueous solution for a time sufficient to lodge the at least one media strip within the first cassette.

26. The method of claim 25, wherein the aqueous solution comprises a sample to be separated in the media.

27. The method of claim 22, further comprising a later step of removing the plurality of electrophoretic separation media from the first cassette.

28. The method of any one of claims 22 to 27, wherein the electrophoretic separation media has an immobilized pH gradient.

29. A system for performing electrophoresis, comprising:
  a buffer core according to claim 20;
  at least one means for enclosing a plurality of electrophoretic separation media, said enclosing means configured to operationally contact the buffer core; and
  means for enclosing said buffer core and said enclosing means.

30. The system of claim 29, wherein the electrophoretic separation media are prior-cast hydratable media strips.

31. The system of claim 30, wherein the at least one means for enclosing a plurality of electrophoretic separation media is capable of hydratingly lodging the strips within.

32. The system of claim 29, wherein the at least one means for enclosing a plurality of electrophoretic separation media permits spaced electrical communication with each of the enclosed media.

33. A method for performing electrophoresis, comprising:
  engaging a first cassette in operational contact with the first engagement face of a buffer core according to claim 21,
  engaging a second cassette in operational contact with the second engagement face of the buffer core, wherein the first and the second cassettes each encloses at least one electrophoretic separation medium and permits spaced electrical communication with each of the enclosed media; and
  establishing a voltage gradient in the enclosed media sufficient to effect electrophoretic separation of analytes within each of the media.

34. A method for performing electrophoresis, comprising:
  hydratingly lodging at least one prior-cast hydratable electrophoretic separation medium within an enclosing member, the enclosing member comprising a plurality of channels, each channel comprising a first channel entry and a second channel entry, wherein
    the entries permit spaced electrical communication with at least one of the at least one enclosed medium and at least one of the entries is dimensioned to allow insertion therethrough of the at least one prior-cast hydratable electrophoretic separation medium in its dehydrated state into one of the plurality of channels of the enclosing member; and then
    using said spaced electrical communication to establish a voltage gradient in at least one of the enclosed medium sufficient to effect electrophoretic separation of analytes therein.

35. The method of claim 32, wherein at least one of the plurality of channels has a width of 3.0 mm to 4.1 mm.

36. The method of claim 35, wherein the at least one prior-cast hydratable electrophoretic separation medium has an immobilized pH gradient.

* * * * *